(12) United States Patent
Xiang et al.

(10) Patent No.: US 7,825,110 B2
(45) Date of Patent: Nov. 2, 2010

(54) SUBSTITUTED SPIROHETEROCYCLES

(75) Inventors: Min A. Xiang, Bridgewater, NJ (US); Mona Patel, Belle Mead, NJ (US); Philip Rybczynski, Somerville, NJ (US); Joseph Gunnet, Flemington, NJ (US); Keith T. Demarest, Flemington, NJ (US); Richard Look, Trenton, NJ (US); Bruce Maryanoff, Forest Grove, PA (US); Michael J. Costanzo, Ivyland, PA (US); Stephen C. Yabut, Perkasie, PA (US)

(73) Assignee: Janssen Pharmaceutica NV (BE)

( * ) Notice: Subject to any disclaimer, the term of this patent is extended or adjusted under 35 U.S.C. 154(b) by 395 days.

(21) Appl. No.: 11/857,891

(22) Filed: Sep. 19, 2007

(65) Prior Publication Data

US 2008/0076753 A1    Mar. 27, 2008

Related U.S. Application Data

(60) Provisional application No. 60/826,654, filed on Sep. 22, 2006.

(51) Int. Cl.
*A61P 9/00* (2006.01)
*A61K 31/55* (2006.01)
*C07D 223/14* (2006.01)

(52) U.S. Cl. .................. 514/212.02; 540/543
(58) Field of Classification Search ............ 514/212.02; 540/543
See application file for complete search history.

(56) References Cited

U.S. PATENT DOCUMENTS

| | | |
|---|---|---|
| 4,617,302 A | 10/1986 | Robertson |
| 5,258,510 A | 11/1993 | Ogawa et al. |
| 5,559,230 A | 9/1996 | Ogawa et al. |
| 5,663,431 A | 9/1997 | Di Malta et al. |
| 5,686,624 A | 11/1997 | Di Malta et al. |
| 5,726,322 A | 3/1998 | Di Malta et al. |
| 5,728,723 A | 3/1998 | Di Malta et al. |
| 5,849,780 A | 12/1998 | Di Malta et al. |
| 5,985,869 A | 11/1999 | Ogawa et al. |
| 7,001,898 B2 | 2/2006 | Chen et al. |

FOREIGN PATENT DOCUMENTS

| | | |
|---|---|---|
| EP | 0636608 A | 2/1995 |
| EP | 0640592 A | 3/1995 |
| EP | 0640592 B1 | 3/1995 |
| WO | WO 9105549 A | 5/1993 |
| WO | WO 9407496 A | 4/1994 |
| WO | WO 9525443 A | 9/1995 |
| WO | WO 9749707 A | 12/1997 |
| WO | WO 9937637 A | 7/1999 |
| WO | WO 02/02531 | 1/2002 |
| WO | WO 2005/000819 | 1/2005 |
| WO | WO 2005/037795 | 4/2005 |
| WO | WO 2007/084591 | 7/2007 |

OTHER PUBLICATIONS

Ali et al., Therapeutic Potential of Vasopressin Receptor Antagonists, Drugs, vol. 67, No. 6, pp. 847-858, 2007.*
Van Zwieten, P.A. "Compensatory Mechanisms Associated with Congestive Heart Failure as Targets for Drug Treatment". *Progr. Pharmacol. Clin. Pharmacol*, 1990, vol. 7; pp. 49-54.
Fujisawa, G. et al. "Theurapeutic Efficacy of Non-peptide ADH Antagonist OPC-31260 in SIADH rats". *Kidney Intl.*, 1993, vol. 44, pp. 19-23.
Ogawa, H. et al. Orally Active, Nonpeptide Vasopressin $V_2$ Receptor Antagonists: A Notel Series of 1-[4-(Benzoylamino)benzoyl]-2,3,4,5-tetrahydro-1H-benzazepines and Related Compounds. *J. Med. Chem.*, 1996, vol. 39, pp. 3547-3555.
Liebsch, G. et al. "Septal Vasopressin Modulates Anxiety-related behaviour in rats". *Neuroscience Letters*, 1996, vol. 217, pp. 101-104.
Yatsu, T., et al., "Pharmacological Profile of YM087, a novel nonpeptide dual vasopresin $V_{1A}$ and $V_2$ receptor Antagonists, in dogs", *European Journal of Pharmacology*, 1997, 231, pp. 225-230, Elsevier Science B.V.

(Continued)

*Primary Examiner*—Brenda L Coleman
(74) *Attorney, Agent, or Firm*—Jeremy K. McKown

(57) ABSTRACT

The invention is directed to nonpeptide substituted spiroheterobenzazepine of Formula I,

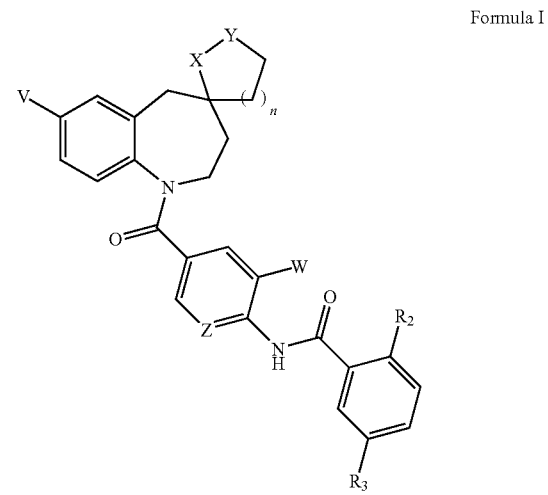

Formula I which are useful as vasopressin receptor antagonists for treating conditions associated with vasopressin receptor activity such as those involving increased vascular resistance and cardiac insufficiency, including congestive heart failure, hyponatremia, and hypertension. Pharmaceutical compositions comprising a compound of Formula I and methods of treating conditions such as hypertension, congestive heart failure, cardiac insufficiency, coronary vasospasm, cardiac ischemia, liver cirrhosis, hyponatremia, renal vasospasm, renal insufficiency, renal failure, diabetic nephropathy, cerebral edema, cerebral ischemia, stroke, thrombosis, or water retention are also disclosed.

25 Claims, No Drawings

OTHER PUBLICATIONS

Yamamura. Y., et al.,"OPC-41061, a Highly Potent Human Vasopressin $V_2$-Receptor Antagonist: Pharmacological Profile Aquaretic Effect by Single and Multiple Oral Dosing in Rats", *The Journal of Pharmacology and Experimental Therapeutics*, 1998, vol. 287, No. 3, pp. 860-867, Second Tokushima Institute of New Drug Research et al., Japan.

Albright D. J., et al., 5-Fluoro-2-methyl-N-[4-(5H-pyrrolo2,1-c-1,4]benzodiazepine-10(11H)-ylcarbonyl)-3-Orally Active Arginine Vasopressin Antagonist with Selectivity for $V_2$ Receptor, *J. Med. Chem.*, 1998, 41, pp. 2442-2444, American Chemical Society.

Ohkawa, T. et al.; "Synthesis and Characterization of Orally Active Nonpeptide Vasopressin V2 Receptor Antagonists". 1999, *Chem. Pharm. Bull.* 47(4) 501-510, Pharm. Society of Japan.

Kondo, K., et al., "7-Chloro-5-hydroxy-1-[2-methyl-4-(2-methylbenzoyl-amino) benzoyl]-2,3,4,5-tetrahydro-1H-1-benzoazepine (OPC-41061): A Potent, Orally Active Nonpeptide Arginine Vasopressin $V_2$ Receptor Antagonist", *Bioorganic & Medicinal Chemistry* 7, 1999, pp. 1743-1754, Second Tokushima Institute of New Drug Research, Otsuka Pharmaceutical Co., Ltd., Japan.

Matschisa, A. et al., "Nonpetide Arginine Vasopressin Antagonists for Both $V_{1A}$ and $V_2$ Receptor: Synthesis and Pharmacological Properties of 4'-[5-(Substituted Methylidene)-2,3,4,5-tetrahydro-1H-1-benzoazepine-1-carbonyl]benzanilide and 4'-{5-(Substituted Methyl)-2,3-dihydro-1H-1-benzoazepine-1-carbonyl]benzanilide Derivatives", Pharmaceutical Society of Japan 1999, *In stitute for Drug Discovery Research*, Yamanouchi Pharmaceutical Co., Ltd., Japan.

Ashwell, M.A., et al., "The Design, Synthesis and Physico-chemical Properties of a Novel Series of Human Vasopressin $V_2$ Receptor Antagonists", *Wyeth-Ayerst Research*, Princeton, New Jersey, 2000.

Kondo, K., et al., "Novel Design of Nonpeptide AVP $V_2$ Receptor Agonists: Structural Requirements for an Agonist Having 1-(4-Aminobenzoyl)-2,3,4,5-tetrahydro-1H-1-benzazepine as a Template", *J. Med. Chem.*, 2000, 43, pp. 4388-4397, American Chemical Society.

Venkatesan H., et al., Total Synthesis of SR 121463 A, a Highly Potent and Selective Vasopressin V2 Receptor Antagonist, *The Journal of Organic Chemistry*, 2001, vol. 66, No. 11, pp. 3653-3661, American Chemical Society.

Xiang, M.A. et al. "Synthesis and Evaluation of Spirobenzazepines as Potent Vasopressin Receptor Antagonists". *Bioorganic & Med. Chemistry Letters*, 2004, vol. 14, No. 11, Jun. 7, pp. 2987-2989. XP004841329.

Xiang, M.A. et al. "Synthesis and Evaluation of Nonpeptide Substituted Spirobenzazepines As Potent Vasopressin Antagonists". *Bioorganic & Med. Chemistry Letters*, 2004, vol. 14, No. 12, Jun. 21, pp. 3143-3146. XP004841361.

Xiang, et al. "Next-Generation Spirobenzazepines: Identification of RWJ-676070 as a Balanced Vasopressin V1a/V2 Receptor Antagonist for Human Clinical Studies". *Bioorganic & Med.I Chemistry Letters*, 2007, vol. 17, No. 23, pp. 6623-6628. XP022325949.

Dusza, J. P., et al., "Way-VNA-932: The First Orally Active, Nonpeptide, Vasopressin V2-Receptor Selective Agonist", *Wveth-Averst Research*, Princeton, New Jersey, 2000.

Shumsky, J. S., et al., "Pyridobenzodiazepines: Synthesis and Structure-Activity Relationships of a Novel Class of Orally Active Vasopression $V_2$ Receptor", *Chemical Science Wyeth-Ayerst Research*, Princeton, N.J., 2000.

Shimada, Y., et al., "4,4-Difluoro-5-Methylene-2,3,4,5-Tetrahyro-1H-1-Benzazepine Derivatives: Highly Potent and Selective Antagonist of Arginine Vasopressin V1A Receptor", Japan Pharmaceutical Co., Ltd., Japan, 2000.

Aranapakam et al., "5-Fluoro-2-Methyl-N-[5-5H-Pyrrolo[2,1-c][1,4]Benzodiazepine-10(11H)-YL Carbonyl)-2-Pyridinyl]Benzamide (CL-385004) And Analogs As Orally Active Arginine Vasopressin Receptor Antagonists.", Bioorg. Med. Chem. Lett., 1999, vol. 9, pp. 1737-1740.

Berge et al., "Pharmaceutical Salts.", J. Pharm. Sci., 1977, vol. 66(1), pp. 1-19.

McCall et al., "Reactions of methyl anthranilate with ethyl γ-bromobutyrate.", Journal of the Chemical Society (C), 1970, pp. 1126-1128, DOI: 10.1039/J39700001126.

Proctor et al., "Azabenzocycloheptenones. Part XIV. Cyclisation of amino-acid derivatives to tetrahydro-1-benzazepin-5-ones and tetrahydroquinolin-4-ones.", J. Chem. Soc. Perkin Trans 1, 1972, vol. 14, pp. 1803-1808, DOI: 10.1039/P19720001803.

\* cited by examiner

SUBSTITUTED SPIROHETEROCYCLES

CROSS REFERENCE TO RELATED APPLICATION

This application claims the benefit of U.S. Provisional Application No. 60/826,654, filed Sep. 22, 2006, which is incorporated by reference herein.

FIELD OF THE INVENTION

This invention relates to novel nonpeptide substituted spiroheterobenzazepines useful as, for example, vasopressin receptor antagonists.

BACKGROUND OF THE INVENTION

Vasopressin is a nonapeptide hormone that is secreted primarily from the posterior pituitary gland. The hormone effects its actions through the vascular V-1 and renal V-2 receptor subtypes. The functions of vasopressin include contraction of uterine, bladder, and smooth muscle; stimulation of glycogen breakdown in the liver; induction of platelet aggregation; release of corticotropin from the anterior pituitary and stimulation of renal water reabsorption. As a neurotransmitter within the central nervous system (CNS), vasopressin can affect aggressive behavior, sexual behavior, the stress response, social behavior and memory. The V-1a receptor mediates central nervous system effects, contraction of smooth muscle and hepatic glycogenolytic effects of vasopressin, while the V-1b receptor mediates anterior pituitary effects of vasopressin. The V-2 receptor, presumably found only in the kidney, effects the antidiuretic actions of vasopressin via stimulation of adenylate cyclase (Liebsch, G et al *Neurosci.* 1996, 217, 101).

Elevated plasma vasopressin levels appear to play a role in the pathogenesis of congestive heart failure (P. A. Van Zwieten, *Progr. Pharmacol. Clin. Pharmacol.* 1990, 7, 49). As progress toward the treatment of congestive heart failure, nonpeptide vasopressin V-2 receptor antagonists have induced low osmolality aquaresis and decreased peripheral resistance in conscious dogs with congestive heart failure (H. Ogawa, *J. Med. Chem.* 1996, 39, 3547). In certain pathological states, plasma vasopressin levels may be inappropriately elevated for a given osmolality, thereby resulting in renal water retention and hyponatremia. Hyponatremia, associated with edematous conditions (cirrhosis, congestive heart failure, renal failure), can be accompanied by the syndrome of inappropriate secretion of antidiuretic hormone (SIADH). Treatment of SIADH-compromised rats with a vasopressin V-2 antagonist has corrected their existing hyponatremia (G. Fujisawa, *Kidney Int.* 1993, 44(1), 19). Due in part to the contractile actions of vasopressin at its V-1 receptor in the vasculature, vasopressin V-1 antagonists have reduced blood pressure as a potential treatment for hypertension as well. Known vasopressin receptor antagonists have included YM-087 (Yamanouchi); VPA-985, WAY-140288, and CL-385004 (American Home Products); SR-121463(sanofi-Synthelabo); and OPC 31260, OPC 41061, and OPC 21268 (Otsuka).

Thus, vasopressin receptor antagonists are useful as therapeutics in the conditions of inner ear disorders, hypertension, congestive heart failure, cardiac insufficiency, hyponatremia, coronary vasospasm, cardiac ischemia, liver cirrhosis, renal vasospasm, renal insufficiency, renal failure, diabetic nephropathy, cerebral edema and ischemia, stroke, thrombosis, and water retention. Additional conditions may include nephrotic syndrome, central nervous system injuries, dysmenorrhea, aggression, anxiety and obsessive-compulsive disorders.

SUMMARY OF THE INVENTION

In its many embodiments, the present invention provides a novel class of compounds useful as, for example, vasopressin receptor antagonists, methods of preparing such compounds, pharmaceutical compositions comprising one or more such compounds, methods of preparing pharmaceutical compositions comprising one or more such compounds, and methods of treatment, prevention, inhibition or amelioration of one or more diseases associated with the vasopressin receptors using such compounds or pharmaceutical compositions.

In one aspect, the present application discloses a compound having the general structure in Formula I:

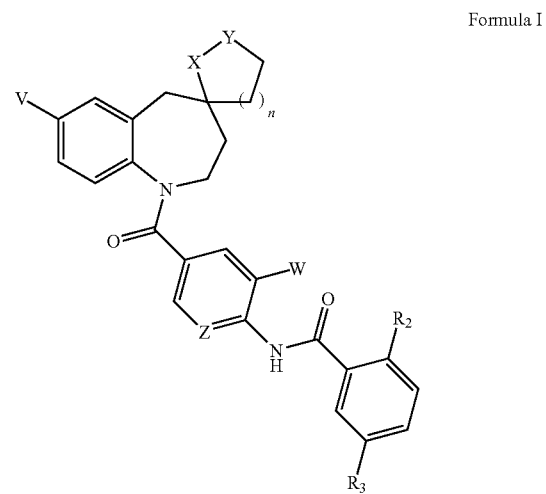

Formula I or pharmaceutically acceptable salts, esters, amides, racemic mixtures, diastereomers and enantiomers thereof wherein:
one of X and Y is $CH_2$ and the other is $NR_1$;
Z is CH or N;
V is H, $C_{1-3}$ alkyl, $C_{1-3}$ alkoxy or halogen;
n=1 or 2,
W is H, $C_{1-3}$ alkoxy, or hydroxy;
$R_1$ is H, $C_{1-5}$ alkyl, arylalkyl, $C_{3-5}$ cycloalkyl, —$CH_2$—C(O)O$R_5$, —C(O)$R_4$, —C(O)($CH_2$)$_m$—N($R_6$)($R_6$), or —C(O)—$CH_2$—C(O)—O$R_5$, where $R_4$ is $C_{1-3}$ alkyl, $R_5$ is H or $C_{1-3}$ alkyl and m is 1 to 3;
$R_2$ is H, halogen, $C_{1-5}$ alkyl, $C_{1-3}$ alkoxy or aryl;
$R_3$ is H, halogen, $C_{1-5}$ alkyl, $C_{1-3}$ alkoxy or aryl; with the proviso that at least one of $R_1$, $R_2$ and $R_3$ is not H; and
the $R_6$ moieties can be the same or different, each being independently selected from the group consisting of H, $C_{1-6}$alkyl, or $C_{3-5}$ cycloalkyl; or alternatively two $R_6$ moieties can be linked together with the N to which they are attached to form a 5 to 6 membered heterocyclyl.

The compounds of the present invention are vasopressin receptor antagonists which are useful, in general, in disease states of inner ear disorders, hypertension, congestive heart failure, cardiac insufficiency, hyponatremia, coronary vasospasm, cardiac ischemia, liver cirrhosis, renal vasospasm, renal insufficiency, renal failure, diabetic nephropathy, cerebral edema and ischemia, stroke, thrombosis, water retention, aggression, obsessive-compulsive disorders, dysmenorrhea, nephrotic syndrome, anxiety and central nervous injuries.

The invention also features a pharmaceutical composition comprising a pharmaceutically acceptable carrier and any of the compounds of Formula I described above, and a pharmaceutical composition made by mixing one or more of the compounds of Formula I and a pharmaceutically acceptable carrier.

The invention also features a process for making a pharmaceutical composition comprising mixing any of the compounds described above and a pharmaceutically acceptable carrier.

The invention further provides methods for using a compound or composition of the invention. For example, one embodiment of the invention is a method for treating a condition associated with vasopressin receptor activity, such as a condition mediated by vasopressin antagonism, in a subject in need thereof comprising administering to the subject a therapeutically effective amount of any of the disclosed compounds or the disclosed pharmaceutical compositions.

Another embodiment of the invention is a method of inhibiting the onset or progression of a condition associated with vasopressin receptor activity in the subject, which comprises administering to the subject a prophylactically effective dose of the pharmaceutical composition of a compound of Formula I.

Other embodiments and features of the invention are disclosed in the following detailed description, examples, and the appended claims.

DETAILED DESCRIPTION OF THE INVENTION

The present invention provides nonpeptide substituted spiroheterobenzazepine compounds which are useful as antagonists of vasopressin receptors. Particularly, these substituted spiroheterobenzazepine compounds inhibit the binding of vasopressin to V-1a, and/or V-2 receptors, and preferably V-1a and V-2 receptors. The compounds of this invention also show functional activity by their ability to inhibit intracellular calcium mobilization and cAMP accumulation induced by arginine vasopressin (AVP) in transfected HEK-293 cells expressing human V-1a and V-2 receptors respectively.

The nonpeptide substituted spiroheterobenzazepine compounds of the present invention are vasopressin receptor antagonists. In a preferred embodiment, the compounds are orally active. In another preferred embodiment, the compounds have the ability to block vasopressin binding to V-1a and V-2. As demonstrated by the results of the pharmacological studies described hereinafter, the compounds show the ability to block vasopressin binding to recombinant V-1a, and/or V-2, and therefore are useful as therapeutics in or prophylactics against conditions such as aggression, obsessive-compulsive disorders, hypertension, dysmenorrhea, hyponatremia, congestive heart failure, cardiac insufficiency, coronary vasospasm, cardiac ischemia, liver cirrhosis, renal vasospasm, renal failure, edema, ischemia, stroke, thrombosis, water retention, nephrotic syndrome, anxiety and central nervous injuries.

Terms

The following terms are defined below and by their usage throughout this disclosure.

"Alkyl" includes an aliphatic hydrocarbon which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of alkyl groups include methyl, ethyl, propyl, isopropyl, n-butyl, isobutyl, t-butyl, 1-methylpropyl, n-pentyl, isopentyl, sec-pentyl, hexyl, heptyl, nonyl, decyl, octyl, fluoromethyl, and trifluoromethyl. For example, $C_4$ alkyl includes but is not limited to n-butyl, isobutyl, and t-butyl. In some embodiments, the alkyl is independently substituted with one to five, preferably one to three groups including, but not limited to, oxo, amino, alkoxy, carboxy, cycloalkyl, nitro, hydroxyl, and halo (F, Cl, Br, or I).

"Alkoxy" includes straight chain, branched, or cyclic alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, SO and $SO_2$. In some embodiments, the alkoxy, aminoalkyl, thioalkyl, and sulfonylalkyl are independently substituted with one to five, preferably one to three groups including, but not limited to, oxo, amino, alkoxy, carboxy, cycloalkyl, nitro, hydroxyl, and halo (F, Cl, Br, or I).

"Aryl" or "Ar" as used herein, whether used alone or as part of a substituent group, includes aromatic groups such as phenyl and naphthyl. When the Ar or aryl group is substituted, it may have one to three substituents which are independently selected from $C_1$-$C_8$ alkyl, $C_1$-$C_8$ alkoxy, aralkoxy, substituted $C_1$-$C_8$ alkyl (e.g., trifluoromethyl), fluorinated $C_1$-$C_8$ alkoxy (e.g., trifluoromethoxy), halogen, cyano, hydroxy, nitro, optionally substituted amino, carboxyl, alkylcarboxyl, alkoxycarbonyl, alkylcarbonyl, arylcarbonyl, $C_1$-$C_4$ alkylamino (i.e., —NH—$C_1$-$C_4$ alkyl), $C_1$-$C_4$ dialkylamino (i.e., —N—[$C_1$-$C_4$ alkyl]$_2$ wherein the alkyl groups can be the same or different), —O(CO)O-alkyl, —O-heterocyclyl optionally substituted with alkyl or alkylcarbonyl (i.e.,

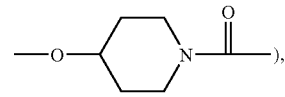), heteroaryl (i.e.,

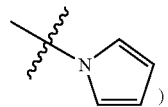)

optionally substituted with a group selected from alkyl, substituted alkyl, aldehyde, alkylcarbonyl, carboxyl, alkylcarboxyl, and alkoxycarbonyl, and unsubstituted, mono-, di- or tri-substituted phenyl wherein the substituents on the phenyl are independently selected from aryl, $C_1$-$C_8$ alkyl, $C_1$-$C_8$ alkoxy, substituted $C_1$-$C_8$ alkyl, fluorinated $C_1$-$C_8$ alkoxy, halogen, cyano, hydroxy, amino, nitro, carboxyl, alkylcarboxyl, alkylamino, dialkylamino and heteroaryl. "Ph" or "PH" denotes phenyl.

"Cycloalkyl" includes a non-aromatic mono- or multicyclic ring system comprising about 3 to about 10 carbon atoms, preferably about 5 to about 10 carbon atoms. Preferred cycloalkyl rings contain about 5 to about 7 ring atoms. Nonlimiting examples of suitable monocyclic cycloalkyls include cyclopropyl, cyclopentyl, cyclohexyl, cyclohetpyl and the like. Non-limiting examples of suitable multicyclic cycloalkyls include 1-decalin, norbornyl, adamantly and the like.

"Halo" or "halogen" includes fluoro, chloro, bromo, and iodo, and preferably fluoro or chloro. As a substituent on an alkyl group, with one or more halo atoms, halo can provide mono-, di-, and tri-substituted groups such as trifluoromethyl, trifluoromethoxy, trifluoromethylthio, difluoromethoxy, or fluoromethylthio.

"Heteroaryl" represents a stable aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur alone or in combination. Preferably the heteroaryls contain from one to three heteroatoms selected from N, O and S. Preferred heteroaryls contain about 5 to about 6 ring atoms. The heteroaryl group may be attached at any heteroatom or carbon atom which results in the creation of a stable structure. Examples of heteroaryl groups include, but are not limited to pyridinyl, pyrazinyl, pyridazinyl, pyrimidinyl, thiophenyl, furanyl, imidazolyl, isoxazolyl, oxazolyl, pyrazolyl, pyrrolyl, thiazolyl, thiadiazolyl, triazolyl, tetrazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl or quinolinyl. Preferred heteroaryl groups include pyridinyl, thiophenyl, furanyl and quinolinyl. When the heteroaryl group is substituted, the heteroaryl group may have one to three substituents which are independently selected from $C_1$-$C_8$ alkyl, substituted $C_1$-$C_8$ alkyl, halogen, aldehyde, alkylcarbonyl, aryl, heteroaryl, alkoxy, alkylamino, dialkylamino, arylamino, nitro, carboxyl, alkylcarboxyl, and hydroxy.

"Heterocyclyl" or "heterocycle" is a 3- to 8-member saturated or partially saturated single or fused ring system which consists of carbon atoms and from one to three heteroatoms selected from N, O and S. The heterocyclyl group may be attached at any heteroatom or carbon atom which results in the creation of a stable structure. Examples of heterocyclyl groups include, but are not limited to pyridine, pyrimidine, oxazoline, pyrrole, imidazole, morpholine, furan, indole, benzofuran, pyrazole, pyrrolidine, piperidine, and benzimidazole. "Heterocyclyl" or "heterocycle" may be substituted with one or more independent groups including, but not limited to, H, halogen, oxo, OH, alkyl, substituted alkyl, amino, heteroaryl, aldehyde, alkylcarbonyl, alkoxycarbonyl, carboxyl, alkylcarboxyl, and alkoxy.

"Arylalkyl" or "aralkyl" includes an aryl-alkyl group in which the aryl and alkyl are as previously described. Preferred aralkyls comprise a $C_{1-6}$ alkyl group. Non-limiting examples of suitable aralkyl groups include benzyl, 2-phenethyl and naphthalenylmethyl.

"Aralkoxy" includes an alkoxy group substituted with an aryl group (e.g., benzyloxy).

"Acyl" as used herein, whether used alone or as part of a substituent group, means an organic radical having 1 to 6 carbon atoms (branched or straight chain) derived from an organic acid by removal of the hydroxyl group.

"Ac" as used herein, whether used alone or as part of a substituent group, means acetyl.

The terms "substituted amino" denotes substitution of said group with at least one member selected from alkyl, substituted alkyl, aryl.

Whenever the term "alkyl", "acyl", or "aryl" or either of their prefix roots appear in a name of a substituent (e.g., aralkyl, dialkylamino), it shall be interpreted as including those limitations given above for "alkyl", "acyl", and "aryl." Designated numbers of carbon atoms (e.g., $C_1$-$C_6$) shall refer independently to the number of carbon atoms in an alkyl or cycloalkyl moiety or to the alkyl portion of a larger substituent in which alkyl appears as its prefix root.

"Pharmaceutically acceptable salts, esters, and amides" include carboxylate salts, amino acid addition salts, esters, and amides which are within a reasonable benefit/risk ratio, pharmacologically effective and suitable for contact with the tissues of patients without undue toxicity, irritation, or allergic response. These salts, esters, and amides may be, for example, $C_{1-8}$ alkyl, $C_{3-8}$ cycloalkyl, aryl, $C_{2-10}$ heteroaryl, or $C_{2-10}$ non-aromatic heterocyclic salts, esters, and amides. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl and ethyl esters. Other examples include $C_{1-6}$ alkyl, $C_{1-5}$ alkyl, $C_{1-4}$ alkyl, or $C_{1-3}$ alkyl esters. Representative salts include hydrobromide, hydrochloride, hydroiodide, perchlorate, sulfate, bisulfate, nitrate, acetate, oxalate, valerate, oleate, palmitate, stearate, laurate, borate, boronate, benzoate, lactate, phosphate, tosylate, citrate, maleate, fumarate, succinate, tartrate, naphthylate, mesylate, glucoheptonate, lactiobionate, methanesulfonate, palmoate, salicylate, saccharinnic and laurylsulfonate. These may include alkali metal and alkali earth cations such as sodium, potassium, calcium, and magnesium, zinc, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66: 1-19; "Handbook of Pharmaceutical Salts—Properties, Selection, and Use" P. Heinrich Stahl, Camille G. Wermuth—Eds. Wiley-VCH Publishers, Zurich, Switzerland which are incorporated herein by reference.

Representative pharmaceutically acceptable amides of the invention include those derived from ammonia, primary $C_{1-6}$ alkyl amines and secondary di($C_{1-6}$ alkyl) amines. Dialkylamides have two alkyl groups that may be independently selected (e.g., methylpropylamide). Secondary amines include 5- or 6-membered heterocyclic or heteroaromatic ring moieties such as morpholinyl containing at least one nitrogen atom and optionally between 1 and 2 additional heteroatoms. Preferred amides are derived from ammonia, $C_{1-3}$ alkyl primary amines, and di($C_{1-2}$ alkyl)amines.

"Patient" or "subject" includes mammals such as humans and animals (dogs, cats, horses, rats, rabbits, mice, non-human primates) in need of observation, experiment, treatment or prevention in connection with the relevant disease or condition. Preferably, the patient or subject is a human.

"Composition" includes a product comprising the specified ingredients in the specified amounts as well as any product that results from combinations of the specified ingredients in the specified amounts.

"Therapeutically effective amount" or "effective amount" (or "prophylatically effect amount") means that amount of active compound or pharmaceutical agent that elicits the biological or medicinal response in a tissue system, animal or human that is being sought by a researcher, veterinarian, medical doctor or other clinician, which includes alleviation (or prevention, or delay or inhibition of onset) of the symptoms of the condition or disorder being treated.

The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

"Prophylactically effect amount" means that amount of active compound or pharmaceutical agent that elicits the biological or medicinal response in a tissue system, animal or human that is being sought by a researcher, veterinarian, medical doctor or other clinician, which includes prevention, or delay or inhibition of onset, of the symptoms of the condition or disorder being treated.

With reference to the number of moieties (non-limiting examples(s) include, substituents, groups or rings) in a compound, unless otherwise defined, the phrases "one or more" and "at least one" mean that, there can be as many moieties as chemically permitted, and the determination of the maximum number of such moieties is well within the knowledge of those skilled in the art. Preferably, there are one to three substituents, or more preferably, one to two substituents, with at least one in the para position.

As used herein, the term "composition" is intended to encompass a product comprising the specified ingredients in the specified amounts, as well as any product which results, directly or indirectly, from combination of the specified ingredients in the specified amounts.

The straight line ——— as a bond generally indicates a mixture of, or either of, the possible isomers, non-limiting examples(s) include, containing (R)- and (S)-stereochemistry. For example,

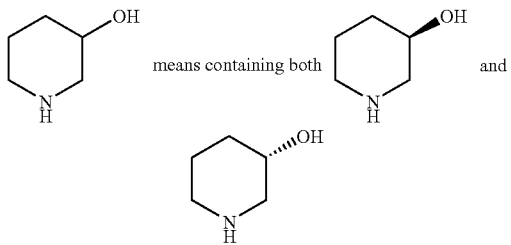

A dashed line (--------) represents an optional bond.
Lines drawn into the ring systems, such as, for example:

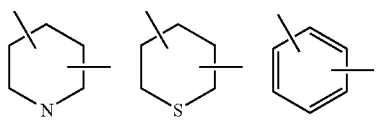

indicate that the indicated line (bond) may be attached to any of the substitutable ring atoms, non limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

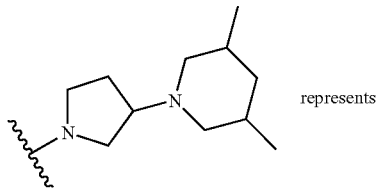

represents

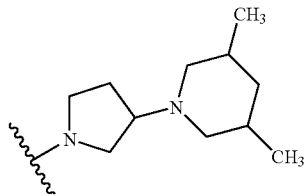

It should be noted that any carbon or heteroatom with unsatisfied valences in the text, schemes, examples, structural formulas, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound Formula I or a salt and/or solvate thereof. A discussion of prodrugs in provided in T. Higuchi and V. Stella, *Pro-drugs ad Novel Delivery Systems* (1987) Volume 14 of the A.C.S. Symposium Series, and *Bioreversible Carriers in Drug Design*, (1987) Edward B. Roched, ed., American Pharmaceutical Association and Pergamon Press, both of which are incorporated herein by reference thereto.

Where the compounds according to this invention have at least one stereogenic center, they may accordingly exist as enantiomers. Where the compounds possess two or more stereogenic centers, they may additionally exist as diastereomers. It is to be understood that all such isomers and mixtures thereof are encompassed within the scope of the present invention.

In one embodiment, the present invention discloses compounds which are represented by structural Formula I, or pharmaceutically acceptable salts, amides, esters, hydrates, solvates, racemic mixtures, diastereomers and enantiomers thereof, wherein the various moieties are as described below.

In an embodiment of Formula I, $R_1$ is methyl, ethyl, benzyl, cyclopentyl, —$CH_2$-cycloalkyl, —$CH_2$—$C(O)OR_5$, —$C(O)R_4$, —$C(O)CH_2$—$N(CH_3)_2$, —$C(O)(CH_2)_m$-heterocyclyl or —$C(O)$—$CH_2$—$C(O)OR_5$.

In an embodiment of Formula I, $R_1$ is —$CH_2$-cyclopropyl.
In an embodiment of Formula I, m is 1 or 2.
In an embodiment of Formula I, $R_1$ is —$C(O)(CH_2)_m$-heterocyclyl and is represented by the following examples:

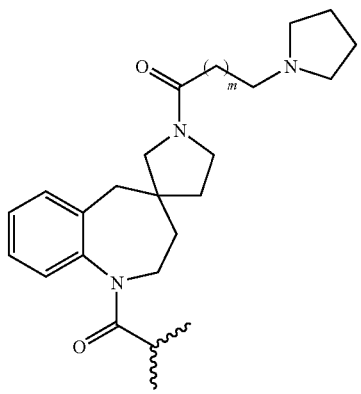

-continued

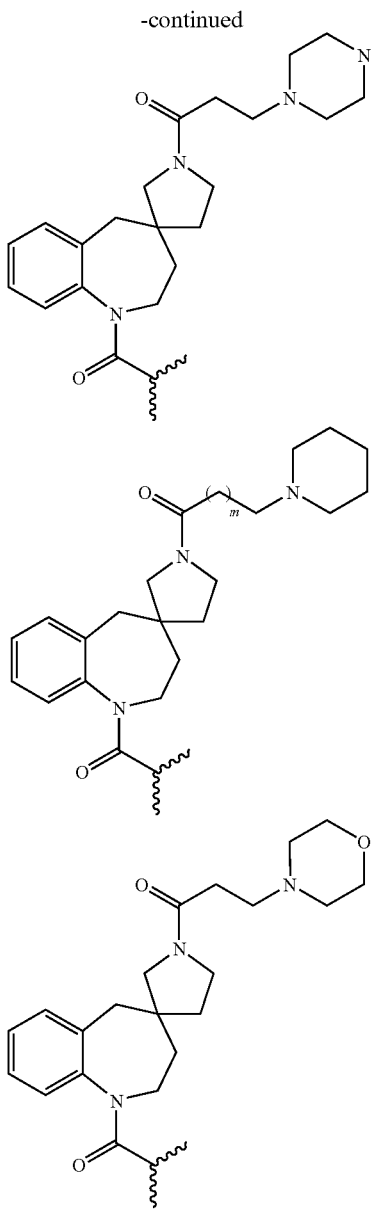

In an embodiment of Formula I, $R_2$ is H, phenyl, —$CH_3$, —$OCH_3$, F or Cl.

In an embodiment of Formula I, $R_2$ is phenyl.

In an embodiment of Formula I, $R_2$ is phenyl and $R_3$ is H.

In an embodiment of Formula I, n is 1.

In an embodiment of Formula I, $R_2$ is phenyl, n is 1, and $R_3$ is H.

In an embodiment of Formula I, $R_3$ is F.

In an embodiment of Formula I, Z is CH.

In an embodiment of Formula I, Z is N.

In an embodiment of Formula I, V is H, —$CH_3$, —$OCH_3$, F or Cl.

In an embodiment of Formula I, V is H.

In an embodiment of Formula I, X is —$CH_2$.

In an embodiment of Formula I, $R_6$ moieties can be the same or different, each being independently selected from the group consisting of H, $C_{1-6}$alkyl, or $C_{3-5}$ cycloalkyl.

In an embodiment of Formula I, $R_6$ moieties can be the same or different, each being independently selected from the group consisting of H or —$CH_3$.

In an embodiment of Formula I, $R_6$ is —$CH_3$.

In an embodiment of Formula I, a compound is selected from the group consisting of:

Benzamide, 2-chloro-N-[4-{(2,3-dihydro-1'-methyl-spiro [4H-1-benzazepine-4,3-piperidin}-1(5H)-yl) carbonyl}phenyl]-5-fluoro;

[1,1'-Biphenyl]-2-carboxamide, N-[4-[(2,3-dihydro-1'-ethyl-spiro{4H-1-benzazepine-4,3'-piperidin}-1(5H)-yl) carbonyl]phenyl}-;

[1,1'-Biphenyl]-2-carboxamide, N-[4-[(2,3-dihydro-1'-methyl-spiro{4H-1-benzazepine-4,3'-piperidin}-1(5H)-yl) carbonyl]phenyl}-;

[1,1'-Biphenyl]-2-carboxamide, N-[4-[(2,3-dihydro-1'-benzyl-spiro{4H-1-benzazepine-4,3'-pyrrolidin}-1(5H)-yl) carbonyl]phenyl}-;

[1,1'-Biphenyl]-2-carboxamide, N-[4-[(2,3-dihydro-spiro{4H-1-benzazepine-4,3'-pyrrolidin}-1(5H)-yl)carbonyl]phenyl}-;

[1,1'-Biphenyl]-2-carboxamide, N-[4-[(2,3-dihydro-1'-cyclopropyl-spiro{4H-1-benzazepine-4,3'-pyrrolidin}-1 (5H)-yl)carbonyl]phenyl}-;

[1,1'-Biphenyl]-2-carboxamide, N-[4-[(2,3-dihydro-1'-methyl-spiro{4H-1-benzazepine-4,3'-pyrrolidin}-1(5H)-yl) carbonyl]phenyl}-;

[1,1'-Biphenyl]-2-carboxamide, N-[4-[(2,3-dihydro-1'-isopropyl-spiro{4H-1-benzazepine-4,3'-pyrrolidin}-1(5H)-yl)carbonyl]phenyl}-;

[1,1'-Biphenyl]-2-carboxamide, N-[4-[(2,3-dihydro-1'-cyclopropylmethyl-spiro{4H-1-benzazepine-4,3'-pyrrolidin}-1(5H)-yl)carbonyl]phenyl}-;

[1,1'-Biphenyl]-2-carboxamide, N-[4-[(2,3-dihydro-1'-acetic acid-spiro{4H-1-benzazepine-4,3'-pyrrolidin}-1(5H)-yl)carbonyl]phenyl}-, methyl ester;

[1,1'-Biphenyl]-2-carboxamide, N-[4-[(2,3-dihydro-1'-acetic acid-spiro{4H-1-benzazepine-4,3'-pyrrolidin}-1(5H)-yl)carbonyl]phenyl}-, ethyl ester;

[1,1'-Biphenyl]-2-carboxamide, N-[4-[(2,3-dihydro-1'-acetic acid-spiro{4H-1-benzazepine-4,3'-pyrrolidin}-1(5H)-yl)carbonyl]phenyl}-;

[1,1'-Biphenyl]-2-carboxamide, N-[4-[(2,3-dihydro-1'-pyruvic acid-spiro{4H-1-benzazepine-4,3'-pyrrolidin}-1(5H)-yl)carbonyl]phenyl}-, ethyl ester;

[1,1'-Biphenyl]-2-carboxamide, N-[4-[(2,3-dihydro-1'-pyruvic acid-spiro{4H-1-benzazepine-4,3'-pyrrolidin}-1(5H)-yl)carbonyl]phenyl}-;

[1,1'-Biphenyl]-2-carboxamide, N-[4-[(2,3-dihydro-1'-acetyl-spiro{4H-1-benzazepine-4,3'-pyrrolidin}-1(5H)-yl)carbonyl]phenyl}-;

[1,1'-Biphenyl]-2-carboxamide, N-[4-[(2,3-dihydro-1'-(N',N'-dimethylaminoethanone-spiro{4H-1-benzazepine-4,3'-pyrrolidin}-1(5H)-yl)carbonyl]phenyl}-;

Benzamide, 2-chloro-N-[4-[(2,3-dihydro-spiro[4H-1-benzazepine-4,2'-piperidin]-1(5H)-yl)carbonyl]phenyl}-5-fluoro-;

[1,1'-Biphenyl]-2-carboxamide, N-[4-[(2,3-dihydro-1'-(phenylmethyl)spiro [4H-1-benzazepine-4,2'-piperidin]-1(5H)-yl)carbonyl]phenyl}-;

[1,1'-Biphenyl]-2-carboxamide, N-[4-[(2,3-dihydrospiro [4H-1-benzazepine-4,2'-piperidin]-1(5H)-yl)carbonyl] phenyl}-;

Benzamide, 2-methyl-N-[4-{(2,3-dihydro-1'-benzyl-spiro [4H-1-benzazepine-4,3-pyrrolidin}-1(5H)-yl) carbonyl}pyridyl]-5-fluoro; and Benzamide, N-[4-{(2,3-dihydro-1'-methyl-spiro[4H-1-benzazepine-4,3-piperidin}-1(5H)-yl)carbonyl}phenyl].

In another embodiment of Formula I, a $V_{1a}$ selective compound is Benzamide, N-[4-{(2,3-dihydro-1'-methyl-spiro [4H-1-benzazepine-4,3-piperidin}-1(5H)-yl) carbonyl}phenyl].

In still another embodiment of Formula I, a compound is selected from the group consisting of:
Benzamide, 2-methyl-N-[4-{(2,3-dihydro-1'-methyl-spiro [4H-1-benzazepine-4,3-piperidin}-1(5H)-yl) carbonyl}phenyl]-5-fluoro;
Benzamide, 2-fluoro-N-[4-{(2,3-dihydro-1'-methyl-spiro [4H-1-benzazepine-4,3-piperidin}-1(5H)-yl) carbonyl}phenyl]-5-fluoro;
Benzamide, 2-methoxy-N-[4-{(2,3-dihydro-1'-methyl-spiro [4H-1-benzazepine-4,3-piperidin}-1(5H)-yl) carbonyl}phenyl]-5-fluoro;
Benzamide, 2-methyl-N-[4-{(2,3-dihydro-1'-methyl-spiro [4H-1-benzazepine-4,3-piperidin}-1(5H)-yl) carbonyl}phenyl]; and
Benzamide, 2-fluoro-N-[4-{(2,3-dihydro-1'-methyl-spiro [4H-1-benzazepine-4,3-piperidin}-1(5H)-yl) carbonyl}phenyl].

In yet another embodiment of Formula I, a compound is selected from:
Benzamide, 2-chloro-N-[4-{(2,3-dihydro-1'-methyl-spiro [4H-1-benzazepine-4,3-piperidin}-1(5H)-yl) carbonyl}phenyl]-5-fluoro;
[1,1'-Biphenyl]-2-carboxamide, N-[4-[(2,3-dihydro-1'-methyl-spiro{4H-1-benzazepine-4,3'-piperidin}-1(5H)-yl) carbonyl]phenyl}-; and
Benzamide, N-[4-{(2,3-dihydro-1'-methyl-spiro[4H-1-benzazepine-4,3-piperidin}-1(5H)-yl)carbonyl}phenyl].

In another aspect of the invention, the compound according to Formula I can be in purified form.

In one embodiment, the invention provides a pharmaceutical composition comprising at least one compound of Formula I in combination with at least one pharmaceutically acceptable carrier or excipient.

In another embodiment, the invention provides a pharmaceutical composition comprising at least one compound selected from:
Benzamide, 2-chloro-N-[4-{(2,3-dihydro-1'-methyl-spiro [4H-1-benzazepine-4,3-piperidin}-1(5H)-yl) carbonyl}phenyl]-5-fluoro;
[1,1'-Biphenyl]-2-carboxamide, N-[4-[(2,3-dihydro-1'-ethyl-spiro{4H-1-benzazepine-4,3'-piperidin}-1(5H)-yl) carbonyl]phenyl}-;
[1,1'-Biphenyl]-2-carboxamide, N-[4-[(2,3-dihydro-1'-methyl-spiro{4H-1-benzazepine-4,3'-piperidin}-1(5H)-yl) carbonyl]phenyl}-;
[1,1'-Biphenyl]-2-carboxamide, N-[4-[(2,3-dihydro-1'-benzyl-spiro{4H-1-benzazepine-4,3'-pyrrolidin}-1(5H)-yl) carbonyl]phenyl}-;
[1,1'-Biphenyl]-2-carboxamide, N-[4-[(2,3-dihydro-spiro{4H-1-benzazepine-4,3'-pyrrolidin}-1(5H)-yl)carbonyl]phenyl}-;
[1,1'-Biphenyl]-2-carboxamide, N-[4-[(2,3-dihydro-1'-cyclopropyl-spiro{4H-1-benzazepine-4,3'-pyrrolidin}-1 (5H)-yl)carbonyl]phenyl}-;
[1,1'-Biphenyl]-2-carboxamide, N-[4-[(2,3-dihydro-1'-methyl-spiro{4H-1-benzazepine-4,3'-pyrrolidin}-1(5H)-yl) carbonyl]phenyl}-;
[1,1'-Biphenyl]-2-carboxamide, N-[4-[(2,3-dihydro-1'-isopropyl-spiro{4H-1-benzazepine-4,3'-pyrrolidin}-1(5H)-yl)carbonyl]phenyl}-;
[1,1'-Biphenyl]-2-carboxamide, N-[4-[(2,3-dihydro-1'-cyclopropylmethyl-spiro{4H-1-benzazepine-4,3'-pyrrolidin}-1(5H)-yl)carbonyl]phenyl}-;
[1,1'-Biphenyl]-2-carboxamide, N-[4-[(2,3-dihydro-1'-acetic acid-spiro{4H-1-benzazepine-4,3'-pyrrolidin}-1(5H)-yl)carbonyl]phenyl}-, methyl ester;
[1,1'-Biphenyl]-2-carboxamide, N-[4-[(2,3-dihydro-1'-acetic acid-spiro{4H-1-benzazepine-4,3'-pyrrolidin}-1(5H)-yl)carbonyl]phenyl}-, ethyl ester;
[1,1'-Biphenyl]-2-carboxamide, N-[4-[(2,3-dihydro-1'-acetic acid-spiro{4H-1-benzazepine-4,3'-pyrrolidin}-1(5H)-yl)carbonyl]phenyl}-;
[1,1'-Biphenyl]-2-carboxamide, N-[4-[(2,3-dihydro-1'-pyruvic acid-spiro{4H-1-benzazepine-4,3'-pyrrolidin}-1(5H)-yl)carbonyl]phenyl}-, ethyl ester;
[1,1'-Biphenyl]-2-carboxamide, N-[4-[(2,3-dihydro-1'-pyruvic acid-spiro{4H-1-benzazepine-4,3'-pyrrolidin}-1(5H)-yl)carbonyl]phenyl}-;
[1,1'-Biphenyl]-2-carboxamide, N-[4-[(2,3-dihydro-1'-acetyl-spiro{4H-1-benzazepine-4,3'-pyrrolidin}-1(5H)-yl)carbonyl]phenyl}-;
[1,1'-Biphenyl]-2-carboxamide, N-[4-[(2,3-dihydro-1'-(N', N'-dimethylaminoethanone-spiro{4H-1-benzazepine-4, 3'-pyrrolidin}-1(5H)-yl)carbonyl]phenyl}-;
[1,1'-Biphenyl]-2-carboxamide, N-[4-[(2,3-dihydrospiro [4H-1-benzazepine-4,2'-piperidin]-1(5H)-yl)carbonyl] phenyl}-;
Benzamide, 2-chloro-N-[4-[(2,3-dihydro-spiro[4H-1-benzazepine-4,2'-piperidin]-1(5H)-yl)carbonyl]phenyl}-5-fluoro-;
[1,1'-Biphenyl]-2-carboxamide, N-[4-[(2,3-dihydro-1'-(phenylmethyl)spiro [4H-1-benzazepine-4,2'-piperidin]-1(5H)-yl)carbonyl]phenyl}-;
Benzamide, N-[4-{(2,3-dihydro-1'-methyl-spiro[4H-1-benzazepine-4,3-piperidin}-1(5H)-yl)carbonyl}phenyl];
Benzamide, 2-methyl-N-[4-{(2,3-dihydro-1'-methyl-spiro [4H-1-benzazepine-4,3-piperidin}-1(5H)-yl) carbonyl}phenyl]-5-fluoro;
Benzamide, 2-fluoro-N-[4-{(2,3-dihydro-1'-methyl-spiro [4H-1-benzazepine-4,3-piperidin}-1(5H)-yl) carbonyl}phenyl]-5-fluoro;
Benzamide, 2-methoxy-N-[4-{(2,3-dihydro-1'-methyl-spiro [4H-1-benzazepine-4,3-piperidin}-1(5H)-yl) carbonyl}phenyl]-5-fluoro;
Benzamide, 2-methyl-N-[4-{(2,3-dihydro-1'-methyl-spiro [4H-1-benzazepine-4,3-piperidin}-1(5H)-yl) carbonyl}phenyl]; and
Benzamide, 2-fluoro-N-[4-{(2,3-dihydro-1'-methyl-spiro [4H-1-benzazepine-4,3-piperidin}-1(5H)-yl) carbonyl}phenyl].

In another embodiment, the invention provides a method for treating a disease or a condition mediated by vasopressin, said method comprising the step of administering to a patient in need of such treatment a therapeutically effective amount of a composition comprising at least one compound of Formula I.

In still another embodiment, the invention provides a method for treating a disease mediated by vasopressin through the vasopressin receptor, said method comprising the step of administering to a patient in need of such treatment a therapeutically effective amount of a composition comprising a vasopressin antagonist.

The yet another embodiment, the invention provides a method for treating a disease mediated by vasopressin through the vasopressin receptor, said method comprising the step of administering to a patient in need of treatment a therapeutically effective amount of a composition comprising a vasopressin 1a ($V_{1a}$), or a vasopressin 2 ($V_2$) antagonist, or an antagonist of both $V_{1a}$ and $V_2$.

In one embodiment, the invention provides a method of inhibiting the onset or progression of a disease or condition associated with vasopressin receptor activity in a patient in need of such treatment the method comprising administering to the patient a prophylactically effective dose of at least one compound according to Formula I.

In one embodiment, the invention provides a method of inhibiting the onset or progression of a disease or condition associated with vasopressin receptor activity in a patient in need of such treatment the method comprising administering to the patient a prophylactically effective dose of at least one compound according to Formula I wherein said compound is a vasopressin antagonist.

In another embodiment of the invention, the vasopressin antagonist comprises a vasopressin 1a ($V_{1a}$), or a vasopressin 2 ($V_2$) antagonist, or an antagonist of both $V_{1a}$ and $V_2$.

In one embodiment, the invention provides a method of treating a condition selected from inner ear disorders, hypertension, congestive heart failure, cardiac insufficiency, coronary vasospasm, cardiac ischemia, liver cirrhosis, renal vasospasm, renal insufficiency, renal failure, diabetic nephropathy, hyponatremia, cerebral edema, cerebral ischemia, stroke, thrombosis, water retention, aggression, obsessive-compulsive disorders, dysmenorrhea, nephrotic syndrome, anxiety and central nervous injuries in a subject in need thereof, such method comprising administering to the subject a therapeutically effective amount of any of the compounds or pharmaceutical compositions described above. Preferably, the disease state is selected from hypertension, congestive heart failure, cardiac insufficiency, renal insufficiency, and hyponatremia. Preferably, the therapeutically effective amount of the compound administered for treating any of these conditions is about 0.05 to 1 g per day.

In another embodiment the disease or condition is congestive heart failure or cardiac insufficiency.

In still another embodiment the disease or condition is hyponatremia.

In yet another embodiment the disease or condition is hypertension.

In a further embodiment the disease or condition is stroke.

In another embodiment the disease or condition is renal failure.

In another embodiment the disease or condition is renal insufficiency.

In one embodiment the invention provides a process for making a pharmaceutical composition comprising mixing any of the compounds according to Formula I and a pharmaceutically acceptable carrier.

Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms. Related compounds also include compounds of the invention that have been modified to be detectable, e.g., isotopically labelled with $^{18}F$ for use as a probe in positron emission tomography (PET) or single-photon emission computed tomography (SPECT).

The invention also includes disclosed compounds having one or more functional groups (e.g., hydroxyl, amino, or carboxyl) masked by a protecting group. See, e.g., Greene and Wuts, Protective Groups in Organic Synthesis, $3^{rd}$ ed., (1999) John Wiley & Sons, NY. Some of these masked or protected compounds are pharmaceutically acceptable; others will be useful as intermediates. Synthetic intermediates and processes disclosed herein, and minor modifications thereof, are also within the scope of the invention.

Amino Protecting Groups

Protection for the amino group includes, but is not limited to, carbamates, amides, and special —NH protective groups.

Examples of carbamates include, but are not limited to, methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include, but are not limited to, methyl and ethyl, 9-fluorenylmethyl, and 4-methoxyphenacyl.

Substituted Ethyl

Examples of substituted ethyl carbamates include, but are not limited to, 2,2,2-trichloroethyl, 2-phenylethyl, t-butyl, vinyl, allyl, 1-isopropylallyl, benzyl, p-methoxybenzyl, p-nitrobenzyl, p-bromobenzyl, p-chlorobenzyl, 2,4-dichlorobenzyl and diphenylmethyl.

Photolytic Cleavage

Examples of photolytic cleavage include, but are not limited to, m-nitrophenyl, 3,5-dimethoxybenzyl, o-nitrobenzyl, 3,4-dimethoxy-6-nitrobenzyl, and phenyl(o-nitrophenyl)methyl.

Amides

Examples of amides include, but are not limited to, N-formyl, N-acetyl, N-trichloroacetyl, N-trifluoroacetyl, N-phenylacetyl, N-3-phenylpropionyl, N-picolinoyl, N-3-pyridylcarboxamide, N-benzoyl, N-p-phenylbenzoyl, and phthaloyl.

C. SYNTHETIC METHODS

The invention provides methods of making the disclosed compounds according to traditional organic synthetic methods as well as matrix or combinatorial synthetic methods. Schemes 1-4 describe suggested synthetic routes. Using these Schemes, the guidelines below, and the examples, a person of skill in the art may develop analogous or similar methods for a given compound that is within the invention. General guidance regarding synthesis is provided in the next section; specific examples with detailed experimental protocols are provided in Section E Examples. Background information may also be found in WO 02/02531 A1, published on Jan. 10, 2002, and incorporated herein by reference.

One skilled in the art will recognize that synthesis of the compounds of the present invention may be facilitated by purchasing an intermediate or protected intermediate compounds described in any of the schemes disclosed herein. One skilled in the art will further recognize that during any of the processes for preparation of the compounds in the present invention, it may be necessary and/or desirable to protect sensitive or reactive groups on any of the molecules concerned. This may be achieved by means of conventional protecting groups, such as those described in "Protective Groups in Organic Synthesis", John Wiley & Sons, 1999. These protecting groups may be removed at a convenient stage using methods known from the art. $P^1$ and $P^2$ are protecting groups exemplified above. Examples of the described synthetic routes include Schemes 1 through 4 and Synthetic Examples 1 through 44. Throughout the Schemes and Examples substituents $R^1$, $R^2$, $R^3$, and V are as described and defined above. Compounds analogous to the target compounds of these examples can be, and in many cases, have been, made according to similar routes. The disclosed compounds are useful in basic research and as pharmaceutical agents as described in the next section. The preparation of compound I (CAS 54620-98-3) has been described by G. R. Proctor et al in *Journal of the Chemical Society* (C), 1970, 1126-1128; *J. Chem. Soc. Perkin Trans* 1 1972, 14, 1803-1808.

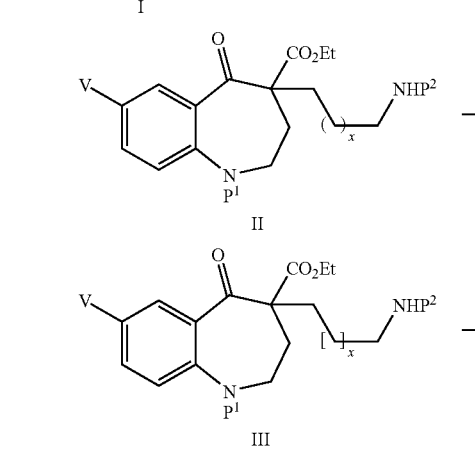

Scheme 1 x = 0, 1

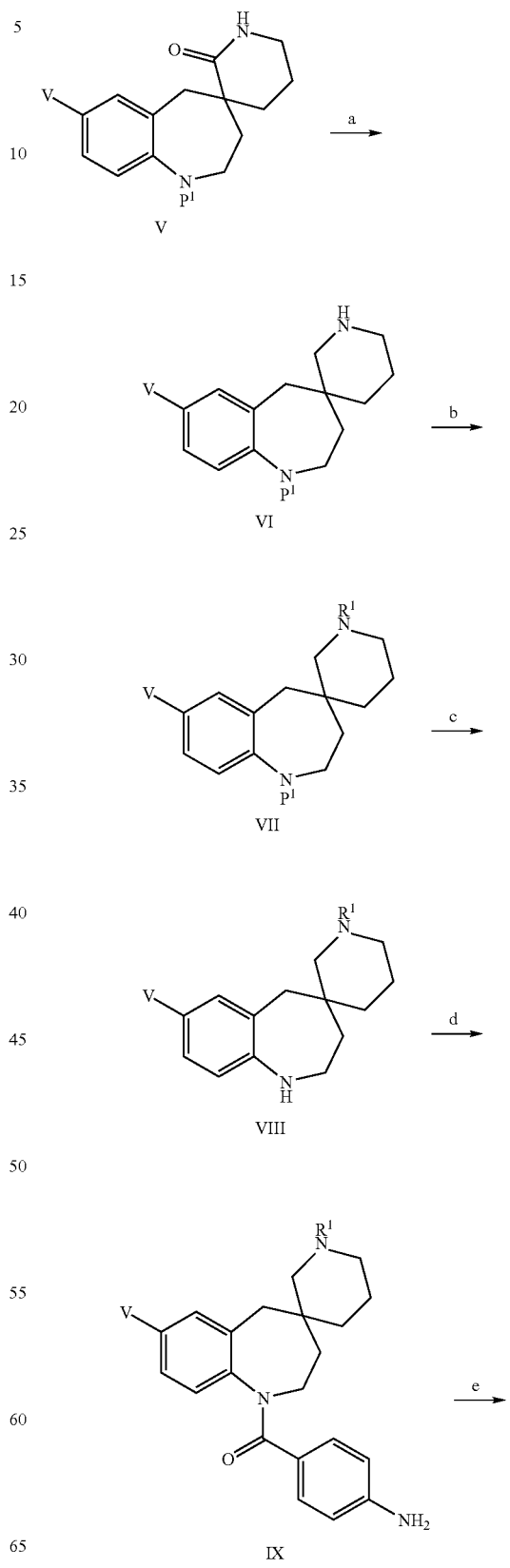

Scheme 2

The compounds of this invention can be prepared by chemistry shown in Scheme 1. A compound of general formula I can be synthesized by methods described in the literature, then alkylated to provide compounds of general formula II, by treatment with an appropriately protected alkylating agent such as N-(3-bromopropyl)phthalimide and a base such as potassium carbonate or sodium carbonate in a solvent such as dimethylformamide at a temperature between ambient and reflux. The carbonyl group in a compound of the general formula II can be reduced under appropriate conditions to the corresponding alkyl compound of the general formula III, by treatment with triethylsilane and trifluoroacetic acid and a Lewis acid such as borontrifluoride etherate at a temperature ranging from 0° C. to ambient. A compound of the general formula III upon warming with hydrazine in an alcoholic solvent such as methanol or ethanol underwent intramolecular cyclization to provide compounds of general formula IV.

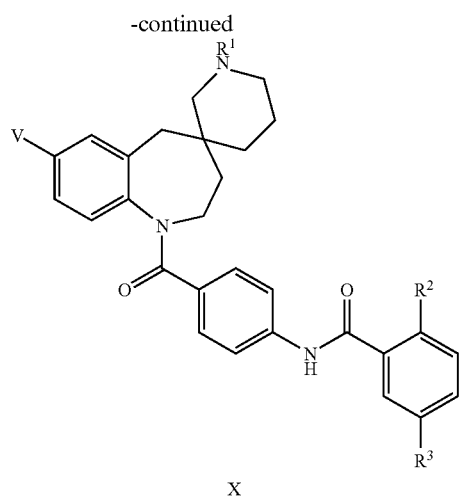

X

A compound of the general formula V can be converted to a compound of the general formula X by methods described in Scheme 2. The amide group in a compound of the general formula V can be reduced to the corresponding amine of general formula VI by treatment with, for instance, a reducing agent such as lithium aluminum hydride in a solvent such as tetrahydrofuran or diethyl ether at temperatures ranging from 0° C. to ambient. A compound of the general formula VI can be alkylated to provide a compound of the general formula VII by treatment with an alkylating agent such as methyl iodide, ethyl iodide, isopropyl iodide or cyclopentyl iodide and an organic base such as triethylamine or diisopropylethylamine in a solvent such as dimethylformamide, at temperatures ranging from 0° C. to ambient. A compound of the general formula VII can be deprotected to provide a compound of the general formula VIII by treatment with, for instance, magnesium turnings in an alcoholic solvent such as methanol or ethanol at a temperature ranging from ambient to 70° C. A compound of the general formula VIII can be acylated upon treatment with an appropriately substituted benzoyl halide such as 4-nitrobenzoyl chloride and an organic base such as triethylamine or diisopropylethylamine in a solvent such as dichloromethane or dichloroethane at a temperature ranging from 0° C. to ambient. The nitro group can be reduced under appropriate conditions to the corresponding amine of the general formula IX, under conditions such as catalytic hydrogenation in a solvent such as ethyl acetate, methanol or ethanol, a catalyst such as palladium on charcoal and hydrogen gas at pressures such as 1 to 20 atmospheres at temperatures ranging from ambient to 60° C. A amine of the general formula IX can be converted to the corresponding amide of the general formula X by treatment with an appropriately substituted benzoyl halide such as 2-chloro-5-fluorobenzoyl chloride and an organic base such as triethylamine or diisopropylethylamine in a solvent such as dichloromethane or dichloroethane at temperatures ranging form 0° C. to ambient.

Scheme 3

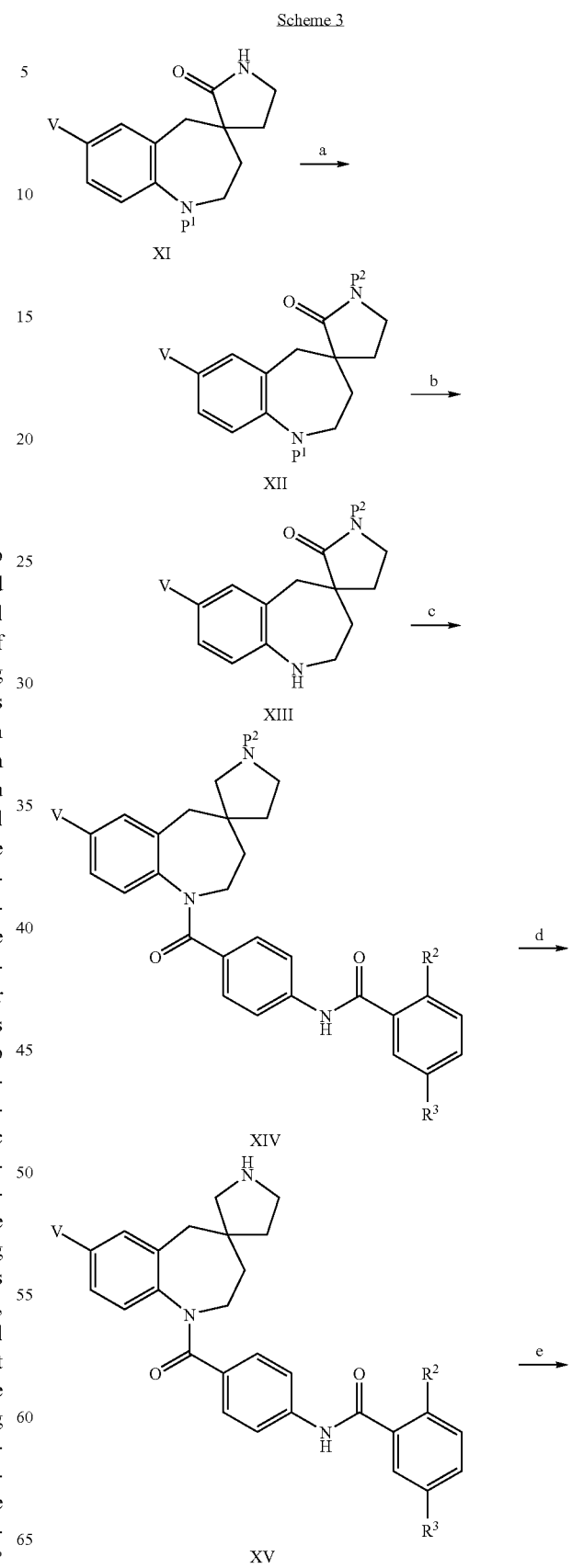

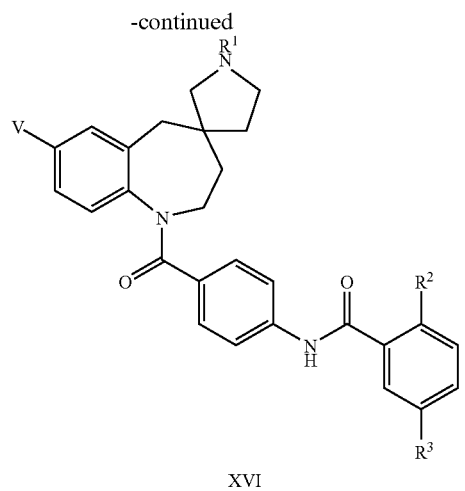

A compound of the general formula XI can be converted to a compound of general formula XVII by methods described in Scheme 3. A compound of general formula XI can be protected to a compound of general formula XII by treatment with, for instance, benzyl bromide and a base such as sodium hydride or potassium hydride in a solvent such as DMF at temperatures ranging from ambient to 70° C. A compound of general formula XII can be converted to a compound of general formula XIII wherein both the removal of a protecting group as well as the reduction of a carbonyl group can be accomplished by treatment with lithium aluminum hydride in a solvent such as diethyl ether or tetrahydrofuran at temperatures ranging from 0° C. to ambient. A amine of the general formula XIII is converted to the corresponding amide of the general formula XIV by treatment with an appropriately substituted benzoyl halide such as 4-[(biphenyl-2-carbonyl)-amino]-benzoyl chloride and an organic base such as triethylamine or diisopropylethylamine in a solvent such as dichloromethane or dichloroethane at temperatures ranging form 0° C. to ambient. A compound of the general formula XIV can be deprotected to a compound of the general formula XV under conditions such as catalytic hydrogenation in a solvent such as ethyl acetate, methanol or ethanol, a catalyst such as palladium on charcoal and hydrogen gas at pressure such as 1 to 20 atmospheres at temperatures ranging from ambient to 60° C. A compound of general formula XV can be converted to a compound of general formula XVI by treatment with, for instance, an alkylating agent such as methyl iodide, ethyl iodide, isopropyl iodide, cyclopropylmethyl iodide or cyclopentyl iodide and an organic base such as triethylamine or diisopropylethylamine in a solvent such as dichloromethane or dichloroethane at temperatures ranging from 0° C. to ambient.

Scheme 4

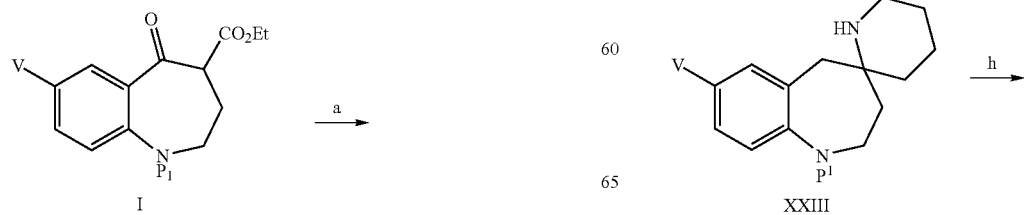

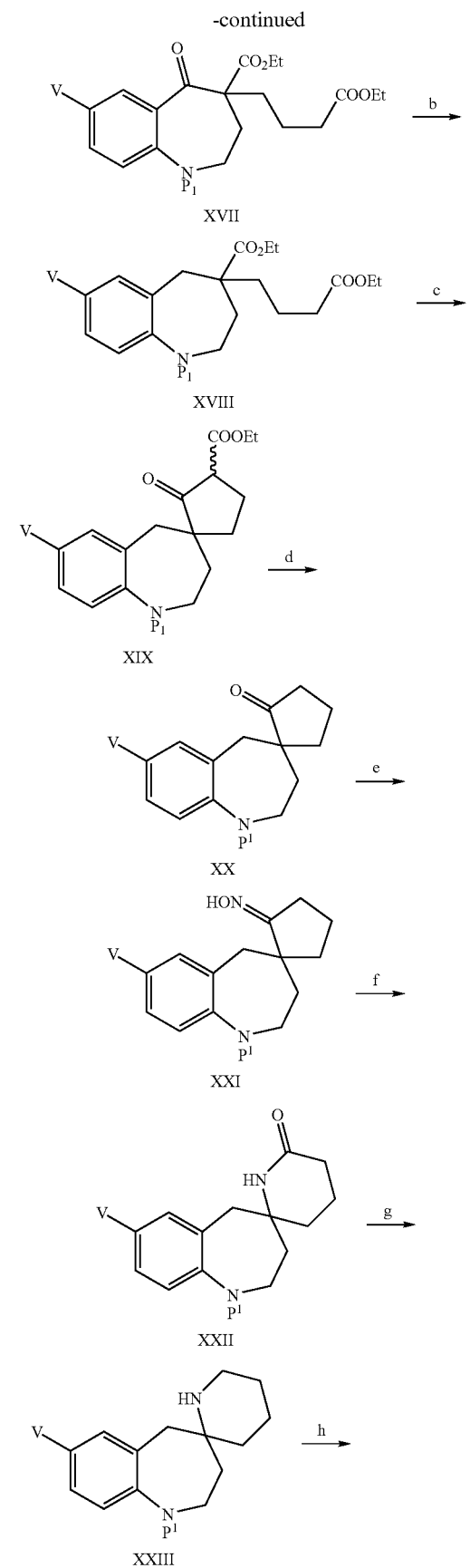

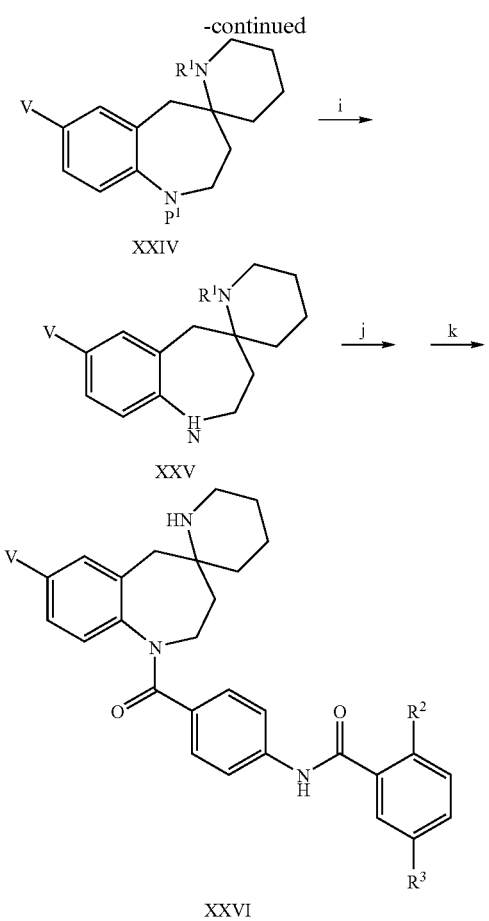

A compound of the general formula I can be converted to a compound of general formula XXVI by methods described in Scheme 4. A compound of general formula I can be converted to a compound of general formula XVII by treatment with an appropriately protected alkylating agent such ethyl 4-bromobutyrate and a base such as potassium carbonate or sodium carbonate in a solvent such as dimethylformamide at temperatures ranging from 0° C. to ambient. A compound of general formula XVII can be converted to a compound of general formula XVIII by treatment with Lewis acid such as boron trifluoride etherate and triethylsilane in a halogenated solvent such as dichloromethane or dichloroethane at temperatures ranging from 5° C. to ambient. A compound of general formula XVIII can be converted to a compound of general formula XIX by treatment with a base such as potassium tert-butoxide in a non-polar solvent such as toluene or xylene at temperatures ranging from 0° C. to ambient. A compound of general formula XIX can be converted to a compound of general formula XX by treatment with glacial acetic acid and 6N hydrochloric acid in alcoholic solvent such as ethanol or isopropanol at temperatures ranging from ambient to reflux. A compound of general formula XX can be converted to a compound of general formula XXI by treatment with hydroxylamine hydrochloride in an alcoholic solvent such as ethanol at temperatures ranging from ambient to reflux. A compound of general formula XXI can be converted to a compound of general formula XXII by treatment with dimethylaminopyridine and p-toluenesulfonyl chloride in a solvent such as pyridine at temperatures ranging from ambient to 65° C. A compound of general formula XXII can be converted to a compound of general formula XXIII by treatment with a reducing agent such as borane-methylsulfide in a solvent such as tetrahydrofuran at temperatures ranging from ambient to reflux. A compound of general formula XXIII can be converted to a compound of general formula XXIV by treatment with formaldehyde, formic acid in an alcoholic solvent such as methanol or ethanol at temperatures ranging from ambient to reflux. A compound of general formula XXIV can be converted to a compound of general formula XXV by treatment with magnesium turnings in an alcoholic solvent such as methanol, ethanol at temperatures ranging from ambient to reflux. A compound of general formula XXV can be converted to a compound of general formula XVI by treatment with an appropriately substituted benzoyl halide such as 4-[(biphenyl-2-carbonyl)-amino]-benzoyl chloride in the presence of base such as triethylamine in a polar solvent such as dimethylformamide at temperatures ranging from 0° C. to ambient.

D. USE AND FORMULATIONS

The compounds of Formula I are useful in the treatment of conditions such as inner ear disorders, hypertension, congestive heart failure, cardiac insufficiency, hyponatremia, coronary vasospasm, cardiac ischemia, liver cirrhosis, renal vasospasm, renal insufficiency, renal failure, diabetic nephropathy, cerebral edema and ischemia, stroke, thrombosis, water retention, aggression, obsessive-compulsive disorders, dysmenorrhea, nephrotic syndrome, anxiety and central nervous injuries. Utility can be investigated according to the procedures known in the art, such as those described herein as Biological Examples 1-5 below. The present invention therefore provides a method of treating any of the above-disclosed conditions in a subject in need thereof, which method comprises administering a compound of Formula I in a pharmaceutically effective amount. The compound may be administered to a patient by any conventional route of administration including, but not limited to, intravenous, oral, subcutaneous, intramuscular, intradermal and parenteral.

The present invention also provides pharmaceutical compositions comprising one or more compounds, such two, three or four, of this invention in association with a pharmaceutically acceptable carrier.

To prepare the pharmaceutical compositions of this invention, one or more compounds of Formula I or, for example, a salt thereof, as an active ingredient(s), is intimately admixed with a pharmaceutical carrier according to conventional pharmaceutical compounding techniques. The form of the carrier depends upon the type of administration, e.g., oral, or parenteral such as intramuscular. In preparing the compositions in oral dosage form, any of the usual pharmaceutical media may be employed. Thus, for liquid oral preparations such as suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are generally employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1 mg to 1 g of active agent(s). Nonlimiting examples include 0.2 mg, 0.5 mg, 0.75 mg, 1 mg, 1.2 mg, 1.5 mg, 2 mg, 3 mg, 5 mg, 7 mg, 10 mg, 25 mg, 50 mg, 100 mg, 250 mg, and 500 mg dosages. The dosages, however, may be varied depending upon the requirement of the patients, the severity of the condition being treated and the compound being employed. The use of either daily administration or post-periodic dosing may be employed.

Preferably these compositions are in unit dosage form such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg or more of the active ingredient of the present invention. The tablets or pills of the disclosed compositions can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific or enantioselective synthesis, or by resolution. The compounds may, for example, be resolved into their components enantiomers by standard techniques, such as the formation of diastereomeric pairs by salt formation. The compounds may also be resolved by formation of diastereomeric esters or amides, followed by chromatographic separation and removal of the chiral auxiliary. Alternatively, the compounds may be resolved using a chiral HPLC column.

Advantageously, compounds of the present invention may be administered in a single daily dose, or the total daily dosage may be administered in divided doses of two, three or four times daily, once-weekly, biweekly, or once monthly. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms can be in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders of vascular resistance is required.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following examples are intended to illustrate the invention but not to limit it.

E. EXAMPLES

Example 1

4-[3-(1,3-Dioxo-1,3-dihydro-isoindol-2-yl)-propyl]-5-oxo-1-(toluene-4-sulfonyl)-2,3,4,5-tetrahydro-1H-benzo[b]azepine-4-carboxylic ethyl ester (1)

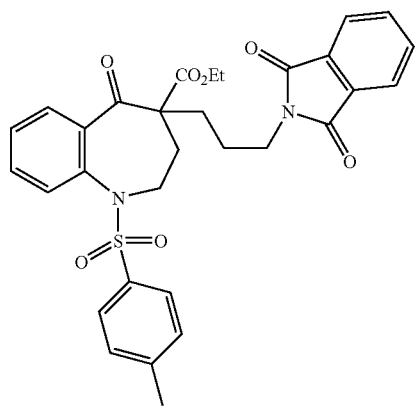

To a solution of 1H-1-Benzazepine-4-carboxylic acid, 2,3,4,5-tetrahydro-1-[(4-methylphenyl)sulfonyl]-5-oxo-, ethyl ester (6.5 g, 16.8 mmol) in DMF (100 mL) at 0° C. was added N-(3-bromopropyl)phthalimide (5.4 g, 20 mmol) followed by potassium carbonate (4.64 g, 33.6 mmol) and the resulting reaction mixture was allowed to stir with warming to room temperature for 18 h. The reaction mixture was poured onto 1N HCl and extracted with ether (2×100 mL). The combined ethyl ether extracts were dried over anhydrous sodium sulfate and concentrated in vacuo. Recrystallisation from ethanol provided 4.5 g of 1 as a white solid (9.64 g theoretical, 47% yield). $^1$H NMR (CDCl$_3$) δ 7.8(m, 2H), 7.7(m, 2H), 7.5(m, 2H), 7.35(m, 4H), 7.2(m, 2H), 4.1 (q, J=3Hz, 2H), 3.95-3.90 (m, 1H), 3.65(t, J=4Hz, 2H), 2.45(m, 1H), 2.4(s, 3H), 1.95-1.9(m, 1H), 1.75(m, 1H), 1.65(m, 1H), 1.55-1.45(m, 2H), 1.05(t, J=4Hz, 3H). MS (ES) m/z 597(MNa)$^+$

Example 2

4-[3-(1,3-Dioxo-1,3-dihydro-isoindol-2-yl)-propyl]-5-oxo-1-(toluene-4-sulfonyl) 2,3,4,5-tetrahydro-1H-benzo[b]azepine-4-carboxylic acid ethyl ester (2)

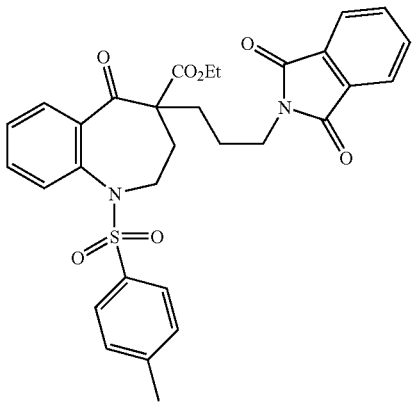

To a solution of phthalimide 1 (3.5 g, 6.1 mmol) in dichloromethane (200 mL) at 0° C. was added triethylsilane (2.79 g, 24 mmol) followed by trifluoromethyl acetic acid (1.39 g, 12.2 mmol). Thereafter BF$_3$.Et$_2$O (1.28 g, 9 mmol) and MeSO$_3$H (0.88 g) were also added and the reaction mixture was allowed to stir at 0° C. for 30 minutes. The reaction mixture was allowed to stir for an additional hour with warming to room temperature. The reaction mixture was poured onto water and extracted with dichloromethane (2×100 mL). The combined dichloromethane extracts washed with saturated NaHCO$_3$ and were dried over anhydrous sodium sulfate to provide 3 g of 2 as a yellow oil (3.42 g theoretical, 88% yield). $^1$H NMR (CDCl$_3$) δ 7.9(m, 2H), 7.75(m, 2H), 7.6(m, 2H), 7.35(m, 2H), 7.15-7.0(m, 4H), 4.05-4.95(m, 2H), 3.6(m, 2H), 2.6(m, 1H), 2.4(m, 1H), 2.35(s, 3H), 2.3-2.2(m, 1H), 2.7-4(m, 5H), 1.1(m, 3H). MS (ES) m/z 561(MH)$^+$

Example 3

Spiro[4H-1-benzazepine-4,3'-piperidin]-2'-one, 1,2,3,5-tetrahydro-1-(4-methylphenylsulfonyl)- (3)

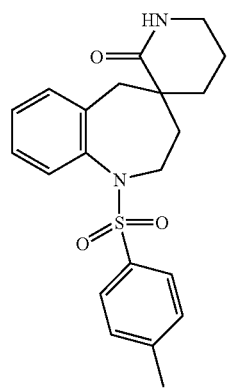

To a solution of 2 (1.5 g, 2.7 mmol) in methanol (120 mL) was added hydrazine (200 mL) and the resulting reaction mixture was allowed to stir at 75° C. for 3 h. The reaction mixture was concentrated in vacuo. Chromatography (SiO$_2$, EtOAc eluant) provided 400 mg of 3 (1.04 g theoretical, 39% yield). $^1$H NMR (CDCl$_3$) δ 7.6(d, J=7Hz, 2H), 7.45(m, 1H), 7.35-7.15(m, 4H), 7.0(m, 1H), 6.15(br s, 1H), 4.35(m, 1H), 3.3(m, 1H), 3.2(m, 2H), 2.65(m, 1H), 2.4(m, 1H), 2.35(s, 3H), 2.2(m, 1H), 2.05(s, 2H), 1.75-1.6(m, 2H), 1.5-1.35(m, 2H), 1.3-1.2(m, 1H). MS (ES) m/z 385(MH)$^+$ Example 4

Spiro[4H-1-benzazepine-4,3'-piperidin], 1,2,3,5-tetrahydro-1-(4-methylphenylsulfonyl)- (4)

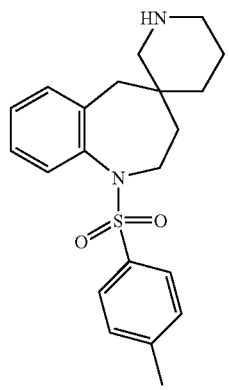

To a solution of compound 3 (1.0 g, 2.6 mmol) in ethyl ether (50 mL) at room temperature was added LAH (198 mg, 5.2 mmol) and the resulting reaction mixture was allowed to stir at room temperature for 24 h. The reaction mixture was quenched with saturated potassium carbonate and extracted with ethyl ether (2×50 mL). The combined ethyl ether extracts were dried over anhydrous sodium sulfate and concentrated in vacuo to provide 800 mg of 4 as an oil (962 mg theoretical, 89% yield). $^1$H NMR (CDCl$_3$) δ 7.65(d, J=7Hz, 2H), 7.35-7.15 (m, 5H), 7.05-7.0(m, 1H), 3.8(m, 1H), 3.65-3.6(m, 1H), 3.55(m, 1H), 3.1(m, 1H), 2.85-2.5(m, 2H), 2.4(s, 3H), 2.3(s, 2H), 2.2(m, 1H), 1.7(m, 1H), 1.55-1.1(m, 2H), 0.85(m, 2H). MS (ES) m/z 371(MH)$^+$ Example 5

Spiro[4H-1-benzazepine-4,3'-piperidin], 1,2,3,5-tetrahydro-1'-methyl-1-(4-methylphenylsulfonyl)- (5)

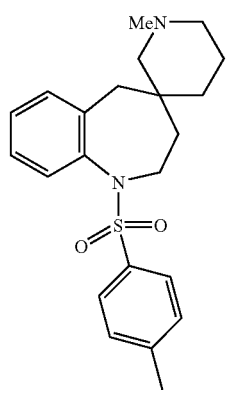

To a solution of 4 (110 mg, 0.30 mmol) in DMF (10 mL) at 0° C. was added TEA (150 mg, 1.5 mmol) followed by methyl iodide (0.2 mL) and the resulting reaction mixture was allowed to stir with warming to room temperature for 2 h. The reaction mixture was poured onto water and extracted with ethyl acetate (3×50 mL). The combined ethyl acetate extracts were dried over anhydrous sodium sulfate and concentrated in vacuo to provide 100 mg of 5 as an oil (107 mg theoretical, 94% yield). $^1$H NMR (CDCl$_3$) δ 7.6(d, J=7Hz, 2H), 7.3-7.15(m 5H), 7.1(m, 1H), 3.8(m, 1H), 3.6(m, 1H), 2.45(s, 3H), 2.35-2.3(m, 2H), 2.2-2.1(m, 2H), 2.1(s, 3H), 1.9(m, 1H), 1.8(m, 1H), 1.7(m, 1H), 1.45-1.35(m, 3H), 1.1(m, 1H), 0.95 (m, 1H). MS (ES) m/z 385(MH)$^+$ Example 6

Spiro[4H-1-benzazepine-4,3'-piperidin], 1,2,3,5-tetrahydro-1'-methyl- (6)

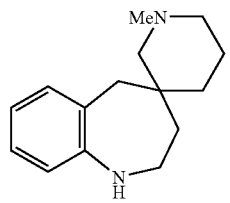

To a solution of 5 (50 mg, 0.14 mmol) in methanol (15 mL) at room temperature was added magnesium turnings (18 mg) and the resulting reaction mixture was allowed to stir at 70° C. for 18 h. The reaction mixture was quenched with saturated ammonium chloride and extracted with ethyl acetate (3×15 mL). The combined ethyl acetate extracts were dried over anhydrous sodium sulfate and dried in vacuo to provide 23 mg of 6 as an oil (1107 mg theoretical, 21% yield). $^1$H NMR (CDCl$_3$) δ 7.0(m, 2H), 6.8(t, J=7Hz, 1H), 6.65(d, J=7Hz, 1H), 3.75(m, 1H), 3.1(m, 2H), 2.95-2.8(m, 1H), 2.6(m, 1H), 2.4-2.15(m, 2H), 2.2(s, 3H), 2.1(m, 1H), 1.8(m, 1H), 1.7-1.5(m, 3H), 1.35-1.25(m, 1H), 1.2-1.1(m, 1H). MS (ES) m/z 231 (MH)$^+$ Example 7

Spiro[4H-1-benzazepine-4,3'-piperidin], 1,2,3,5-tetrahydro-1'-methyl-1-(4-aminobenzoyl)- (7)

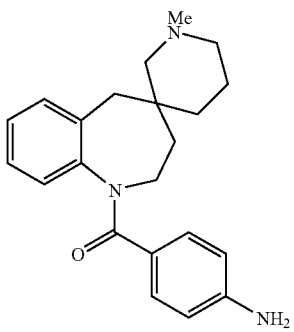

To a solution of 6 (150 mg, 0.65 mmol) in dichloromethane (50 mL) at 0° C. was added TEA (150 mg) followed by 4-nitrobenzoyl chloride (180 mg, 0.98 mmol) and the resulting reaction mixture was allowed to stir with warming to room temperature for 2 h. The reaction mixture was poured onto 1N NaOH and extracted with dichloromethane (2×50 mL). The combined dichloromethane extracts were dried over anhydrous sodium sulfate and dried in vacuo to provide the crude amine. To a solution of the crude nitro compound in methanol (25 mL) was added 10% Pd/C (15 mg) and the resulting reaction mixture was subjected to hydrogenation in a Parr Shaker apparatus for 4 h at 20 psi. The reaction mixture was filtered through Celite and the filtrate concentrated in vacuo to provide 100 mg of 7 as a yellow oil (105 mg theoretical, 95% yield). $^1$H NMR (CDCl$_3$) δ 7.85(m, 1H), 7.2(m, 1H), 7.05(m, 1H), 7.0-6.9(m, 2H), 6.6-6.5(m, 2H), 6.3(d, J=7Hz, 1H), 4.7(m, 1H), 4.5(m, 1H), 4.2(m, 1H), 2.8(m, 1H), 2.5(m, 1H), 2.4(m, 2H), 2.1(m, 2H), 1.7(m, 2H), 2.5(m, 2H). MS (ES) m/z 350(MH)$^+$ Example 8

Benzamide, 2-chloro-N-[4-{(2,3-dihydro-1'-methyl-spiro[4H-1-benzazepine-4,3-piperidin}-1(5H)-yl)carbonyl}phenyl]-5-fluoro (8)

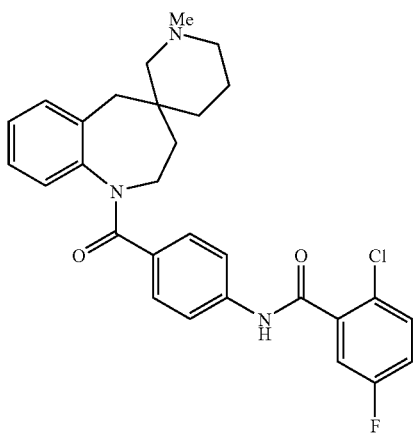

To a solution of 7 (20 mg, 0.06 mmol) in dichloromethane (10 mL) at 0° C. was added TEA (0.25 mL) followed by 2-chloro-5-fluorobenzoyl chloride (22 mg, 0.11 mmol) and the resulting reaction mixture was allowed to stir with warming to room temperature for 2 h. The reaction mixture was poured onto 1N NaOH and extracted with dichloromethane (2×50 mL). The combined dichloromethane extracts were dried over anhydrous sodium sulfate and dried in vacuo. Chromatography (SiO$_2$, 10% MeOH-EtOAc eluant) provided 15 mg of 8 as a white solid (29 mg theoretical, 52% yield). $^1$H NMR (CDCl$_3$) δ 8.1(br s, 1H), 7.45-7.3(m, 2H), 7.2-7.1(m, 3H), 7.1-7(m, 3H), 7.0-6.9(m, 1H), 6.6-6.5(m, 1H), 4.8-4.5(m, 1H), 3.2-3.0(m, 2H), 2.9-2.8(m, 2H), 2.4-2.3(m, 1H), 2.2(br s, 3H), 2.1(br s, 2H), 1.85(m, 1H), 1.8-1.6(m, 2H), 1.6-1.3(m, 2H), 1.0-0.9(m, 1H). MS (ES) m/z 506(m)$^+$ Example 9

[1,1'-Biphenyl]-2-carboxamide, N-[4-[(2,3-dihydro-1'-ethyl-spiro{4H-1-benzazepine-4,3'-piperidin}-1(5H)-yl)carbonyl]phenyl}- (9)

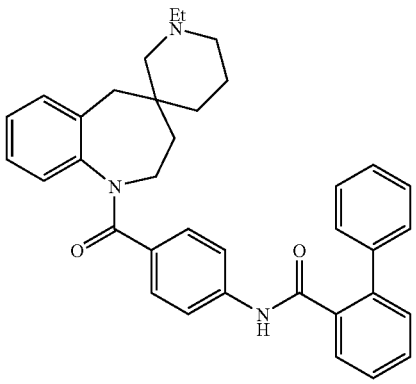

The title compound was prepared from compound 4, ethyl iodide, and biphenyl-2-carbonyl chloride as described in Examples 5-8. $^1$H NMR (CDCl$_3$) δ 7.9(d, J=7Hz, 1H), 7.55-7.45(m, 1H), 7.4-7.3(m, 8H), 7.2(m, 1H), 7.1-7.0(m, 2H), 6.9-6.85(m, 3H), 7.5(m, 1H), 4.75-4.5(m, 1H), 3.2-2.9(m, 2H), 2.85-2.75(m, 1H), 2.65-2.45(m, 1H), 2.4-2.3(m, 2H), 2.25-2.1(m, 1H), 2.1-2.0(m, 1H), 2.85-1.4(m, 6H), 1.05(m, 1H), 0.9(m, 1H). MS (ES) m/z 544(MH)$^+$ Example 10

[1,1'-Biphenyl]-2-carboxamide, N-[4-[(2,3-dihydro-1'-methyl-spiro{4H-1-benzazepine-4,3'-piperidin}-1(5H)-yl)carbonyl]phenyl}- (10)

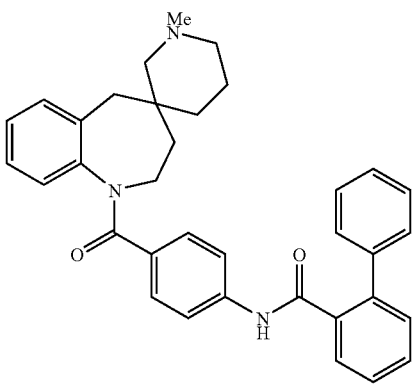

The title compound was prepared from compound 4, methyl iodide, and biphenyl-2-carbonyl chloride as described in Examples 5-8. $^1$H NMR (CDCl$_3$) δ 7.9(d, J=7Hz, 1H), 7.55-7.45(m, 1H), 7.45-7.25(m, 8H), 7.15(m, 1H), 7.1-7.0 (m, 1H), 6.95-6.85(m, 1H), 7.6(m, 1H), 5.85(m, 1H), 4.95(m, 1H), 3.35-3.25(br s, 2H), 2.95-2.8(m, 1H), 2.8-2.7(m, 1H), 2.6-2.45(m, 1H), 1.8-1.7(m, 3H), 1.6(br s, 3H), 1.5-1.35(m, 1H). MS (ES) m/z 530(MH)$^+$

Example 11

4-[2-(1,3-Dioxo-1,3-dihydro-isoindol-2-yl)-ethyl]-5-oxo-1-(toluene-4-sulfonyl)-2,3,4,5-tetrahydro-1H-benzo[b]azepine-4-carboxylic acid ethyl ester (11)

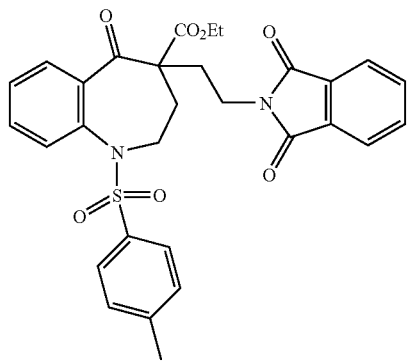

The title compound was prepared from 5-oxo-1-(toluene-4-sulfonyl)-2,3,4,5-tetrahydro-1H-benzo[b]azepine-4-carboxylic acid ethyl ester and N-(2-bromoethyl)phthalimide as described in Example 1. $^1$H NMR (CDCl$_3$) δ 7.85(m, 4H), 7.75(m, 4H), 7.55-7.45(m, 2H), 7.4-7.35(m, 1H), 7.25-7.2 (m, 1H), 4.2-4.0(m, 6H), 3.9-3.85(m, 1H), 3.65-3.55(m, 3H), 3.4(br s, 1H), 2.4(s, 3H), 2.4-2.35(m, 1H), 1.35-1.15(m, 3H). MS (ES) m/z 583(MNa)$^+$

Example 12

4-[2-(1,3-Dioxo-1,3-dihydro-isoindol-2-yl)-ethyl]-1-(toluene-4-sulfonyl)-2,3,4,5-tetrahydro-1H-benzo[b]azepine-4-carboxylic acid ethyl ester (12)

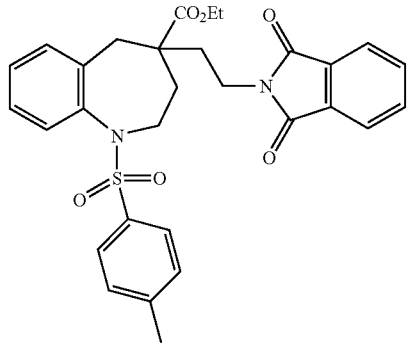

The title compound was prepared from compound II as described in Example 2. $^1$H NMR (CDCl$_3$) δ 7.9-7.85(m, 2H), 7.85-7.8(m, 2H), 7.75-7.65(m, 3H), 7.6(m, 1H), 7.3-7.2 (m, 2H), 7.15-7.0(m, 2H), 4.1(t, J=7Hz, 2H), 4.0-3.85(m, 1H), 3.6(t, J=7Hz, 2H), 2.65-2.5(m, 2H), 2.4(s, 2H), 2.35-2.2 (m, 1H), 2.0-1.9(m, 1H), 1.85-1.65(m, 2H), 1.15(m, J=7Hz, 2H). MS (ES) m/z 569(MNa)$^+$

Example 13

Spiro[4H-1-benzazepine-4,3'-pyrrolidin]-2'-one, 1,2,3,5-tetrahydro-1-(4-methylphenylsulfonyl)- (12)

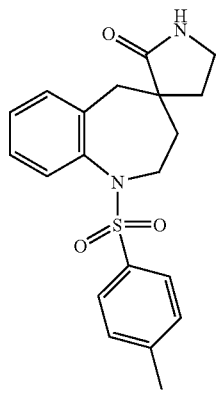

The title compound was prepared from compound 12 as described in Example 3. $^1$H NMR (CDCl$_3$) δ 7.6(m, 2H), 7.35(m, 2H), 7.25-7.2(m, 3H), 7.15-7.1(m, 1H), 4.4-4.3(m, 1H), 3.3-3.15(m, 3H), 2.65(m, 2H), 2.4(s, 3H), 2.3-2.15(m, 4H), 1.75-1.6(m, 2H), 1.6-1.5(m, 1H). MS (ES) m/z 371 (MH)$^+$

Example 14

Spiro[4H-1-benzazepine-4,3'-pyrrolidin]-2'-one, 1,2,3,5-tetrahydro-1'-benzyl-1-(4-methylphenylsulfonyl)- (14)

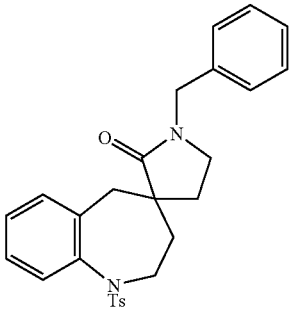

To a solution of protected amide 13 (1.8 g, 4.9 mmol) in DMF at room temperature was added sodium hydride (175 mg, 7.3 mmol) followed by benzyl bromide (1.25 g, 7.3 mmol) and the resulting reaction mixture was allowed to stir at room temperature for 4 h. The reaction mixture was poured onto water and extracted with ethyl acetate (3×100 mL). The combined ethyl acetate extracts were washed with brine and dried over anhydrous sodium sulfate and concentrated in vacuo. Chromatography (SiO$_2$, EtOAc eluant) provided 1.9 g of 14 as a brown oil (2.25 g theoretical, 84% yield). $^1$H NMR (CDCl$_3$) δ 7.6(d, J=8Hz, 2H), 7.4(m, 1H), 7.35-7.25(m, 5H), 7.2-7.1(m, 4H), 7.0(d, J=7Hz, 1H), 4.45-4.3(m, 3H), 3.25-3.15(m, 1H), 3.15-3.0(m, 2H), 2.55(m, 1H), 2.4(s, 3H), 2.3-2.15(m, 2H), 1.65-1.55(m, 1H), 1.55-1.4(m, 2H). MS (ES) m/z 461(MH)$^+$

Example 15

Spiro[4H-1-benzazepine-4,3'-pyrrolidin], 1,2,3,5-tetrahydro-1'-benzyl- (15)

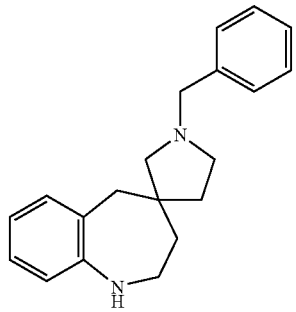

To a solution of protected amide 14 (250 mg, 0.56 mmol) in diethyl ether at 0° C. was added lithium aluminum hydride (85 mg, 2.24 mmol) and the resulting reaction mixture was allowed to stir with warming to room temperature for 16 h. The reaction mixture was poured onto cold, saturated potassium carbonate and extracted with ethyl acetate (3×100 mL). The combined ethyl acetate extracts were washed with brine and dried over anhydrous sodium sulfate and concentrated in vacuo to provide 200 mg of 15 as a white solid (242 mg theoretical, 82%). $^1$H NMR (CDCl$_3$) δ 7.35-7.25(m, 4H), 7.2-7.15(m, 1H), 7.1-7.05(m, 1H), 7.05-6.95(m, 1H), 6.85-6.75(m, 1H), 6.7-6.6(m, 1H), 3.6(d, J=6Hz, 2H), 3.05-2.95 (m, 2H), 2.85-2.75(m, 2H), 2.75-2.65(m, 1H), 2.6-2.5(m, 1H), 2.45-2.4(m, 1H), 2.3-2.3(m, 1H), 1.85-1.75(m, 2H), 1.7-1.6(m, 1H), 1.6-1.45(m, 1H). MS (ES) m/z 293(MH)$^+$

Example 16

[1,1'-Biphenyl]-2-carboxamide, N-[4-[(2,3-dihydro-1'-benzyl-spiro{4H-1-benzazepine-4,3'-pyrrolidin}-1(5H)-yl)carbonyl]phenyl}- (16)

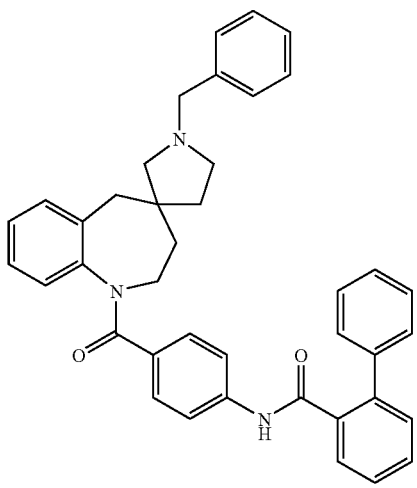

To a solution of amine 15 (180 g, 62 mmol) in dichloromethane at room temperature was added triethylamine (250 mg, 2.48 mmol) followed by 4-[(biphenyl-2-carbonyl)-amino]-benzoyl chloride (310 mg, 0.93 mmol) and the resulting reaction mixture was allowed to stir at room temperature for 16 h. The reaction mixture was concentrated in vacuo. Chromatography (SiO$_2$, 50% EtOAc-Hexanes eluant) provided 120 mg of 16 as a yellow solid (366 g theoretical, 33% yield). $^1$H NMR (CDCl$_3$) δ 7.6(d, J=8Hz, 2H), 7.4(m, 1H), 7.35-7.25(m, 5H), 7.2-7.1(m, 4H), 7.0(d, J=7Hz, 1H), 4.45-4.3(m, 3H), 3.25-3.15(m, 1H), 3.15-3.0(m, 2H), 2.55(m, 1H), 2.4(s, 3H), 2.3-2.15(m, 2H), 1.65-1.55(m, 1H), 1.55-1.4(m, 2H). MS (ES) m/z 461(MH)$^+$

Example 17

[1,1'-Biphenyl]-2-carboxamide, N-[4-[(2,3-dihydrospiro{4H-1-benzazepine-4,3'-pyrrolidin}-1(5H)-yl)carbonyl]phenyl}- (17)

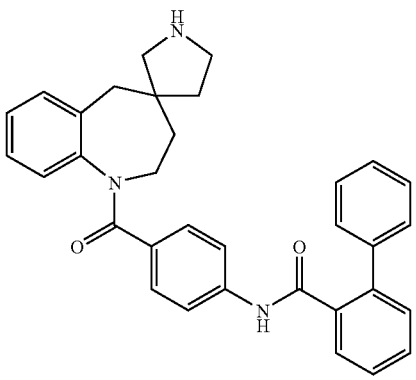

To a solution of 16 (45 mg, 0.1 mmol) in methanol (20 mL) at room temperature was added concentrated HCl (0.25 mL) followed by 25% palladium on carbon (5 mg) and the resulting reaction mixture was subjected to Parr Shaker hydrogenation at 14 psi at room temperature for 3 h. The reaction mixture was filtered through Celite and the filtrate was concentrated in vacuo. The residue was taken up in dichloromethane and washed with saturated sodium bicarbonate and dried over anhydrous sodium sulfate and concentrated in vacuo to provide 40 mg of 17 as a tan solid (50 mg, 80% yield). $^1$H NMR (CDCl$_3$) δ 87.95(d, J=7Hz, 1H), 7.55-7.4(m, 2H), 7.4-7.3(m, 5H), 7.25-7.2(m, 1H), 7.15-7.0(m, 3H), 6.95-6.8(m, 2H), 6.6-6.5(m, 1H), 4.9-4.7(m, 1H), 3.25-3.0(m, 2H), 3.0-2.8(m, 2H0, 2.75-2.5(m, 1H), 2.5-2.1(m, 1H), 2.1-1.95 (m, 1H), 1.95-1.5(m, 2H). MS (ES) m/z 502(MH)$^+$

Example 18

[1,1'-Biphenyl]-2-carboxamide, N-[4-[(2,3-dihydro-1'-cyclopropyl-spiro{4H-1-benzazepine-4,3'-pyrrolidin}-1(5H)-yl)carbonyl]phenyl}- (18)

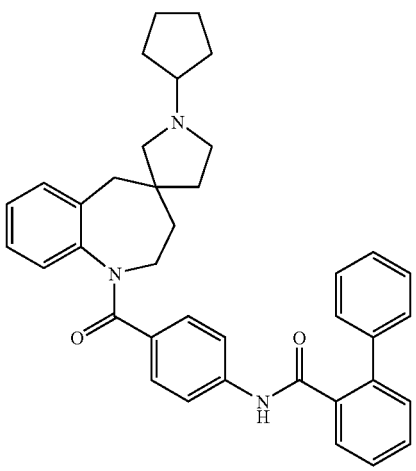

To a solution of 17 (35 mg, 0.07 mmol) in dichloromethane (15 mL) at room temperature was added triethylamine (28 mg, 0.28 mmol) and bromo cyclopentane (21 mg, 0.14 mmol) and the resulting reaction mixture was allowed to stir at room temperature for 1 h. The reaction mixture was poured onto 1N NaOH and extracted with dichloromethane (2×50 mL). The combined dichloromethane extracts were dried over anhydrous sodium sulfate and concentrated in vacuo. Chromatography (SiO$_2$, 5% MeOH-EtOAc eluant) provided 18 as a white solid (39 mg theoretical, 66% yield). $^1$H NMR (CDCl$_3$) δ 7.85 (d, J=7Hz, 1H), 7.5(m, 1H), 7.4(m, 1H), 7.4-7.25(m, 5H), 7.15-7.05(m, 2H), 7.0-6.95(m, 2H), 6.9-6.8(m, 4H), 6.6-6.5(m, 1H), 5.0-4.5(m, 1H), 3.7-3.6(m, 1H), 3.55-3.45(m, 1H), 3.3-3.0(m, 3H), 2.7-2.35(m, 3H), 2.0-1.9(m, 1H), 1.85-1.6(m, 5H), 1.55-1.4(m, 3H), 0.95-0.8(m, 1H). MS (ES) m/z 570(MH)$^+$ Example 19

[1,1'-Biphenyl]-2-carboxamide, N-[4-[(2,3-dihydro-1'-methyl-spiro{4H-1-benzazepine-4,3'-pyrrolidin}-1(5H)-yl)carbonyl]phenyl}- (19)

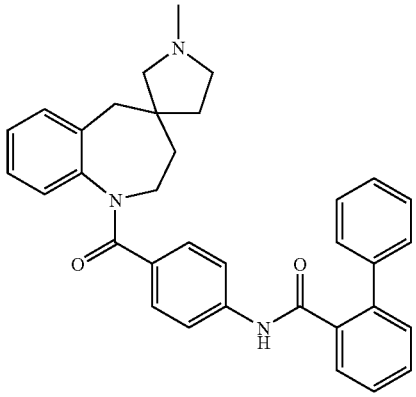

The title compound was prepared from compound 17 and methyl iodide as described in Example 18. $^1$H NMR (CDCl$_3$) δ 7.9(d, J=7Hz, 1H), 7.55-7.2(m, 9H), 7.1-7.05(m, 1H), 7.05-7.0(m, 2H), 6.95(m, 6.8(m, 3H), 6.6-6.5(m, 1H), 1.95-4.7(m, 1H), 3.2-3.1(m, 1H), 3.0-2.8(m, 3H), 2.65-2.5(m, 3H), 1.95 (s, 3H), 1.95-1.75(m, 2H), 1.45-1.3(m, 1H). MS (ES) m/z 516(MH)$^+$ Example 20

[1,1'-Biphenyl]-2-carboxamide, N-[4-[(2,3-dihydro-1'-isopropyl-spiro{4H-1-benzazepine-4,3'-pyrrolidin}-1(5H)-yl)carbonyl]phenyl}- (20)

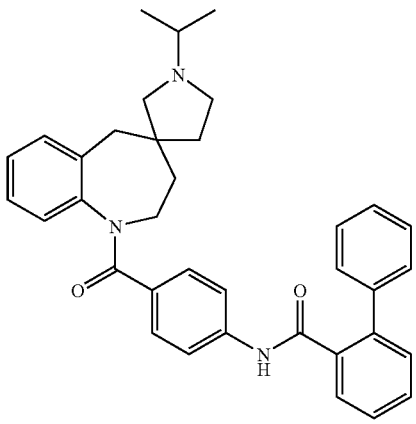

The title compound was prepared from compound 17 and isopropyl iodide as described in Example 18. $^1$H NMR (CDCl$_3$) δ 7.85(d, J=7Hz, 1H), 7.6-7.5(m, 2H), 7.4-7.3(m, 5H), 7.15-7.05(m, 1H), 7.05-6.95(m, 2H), 6.9-6.8(m, 2H), 6.65-6.55(m, 1H), 5.04.75(m, 1H), 3.75-3.6(m, 1H), 3.6-3.45 (m, 1H), 3.3-3.1(m, 2H), 2.7-2.55(m, 1H), 1.8-1.6(m, 3H), 0.95-0.8(m, 1H). MS (ES) m/z 544(MH)$^+$ Example 21

[1,1'-Biphenyl]-2-carboxamide, N-[4-[(2,3-dihydro-1'-cyclopropyl methyl-spiro{4H-1-benzazepine-4,3'-pyrrolidin}-1(5H)-yl)carbonyl]phenyl}- (21)

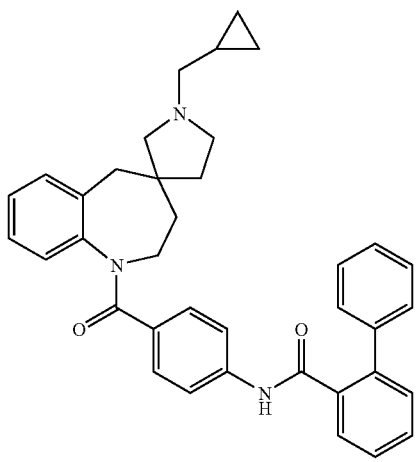

The title compound was prepared from compound 17 and cyclopropylmethyl bromide as described in Example 18. $^1$H NMR (CDCl$_3$) δ 7.85(d, J=7Hz, 1H), 7.6-7.5(m, 2H), 7.35-7.25(m, 5H), 7.25-7.15(m, 1H), 7.1-7.0(m, 2H), 6.95-6.85 (m, 3H), 6.55(d, J=7Hz, 1H), 4.85-4.6(m, 1H), 3.2-3.1(m, 1H), 2.95-1.6(m, 3H), 2.55-2.15(m, 2H), 1.85-1.55(m, 3H), 0.5-0.4(m, 2H), 0.15-0.05(m, 2H). MS (ES) m/z 556(MH)$^+$ Example 22

[1,1'-Biphenyl]-2-carboxamide, N-[4-[(2,3-dihydro-1'-acetic acid-spiro{4H-1-benzazepine-4,3'-pyrrolidin}-1(5H)-yl)carbonyl]phenyl}-, methyl ester (22)

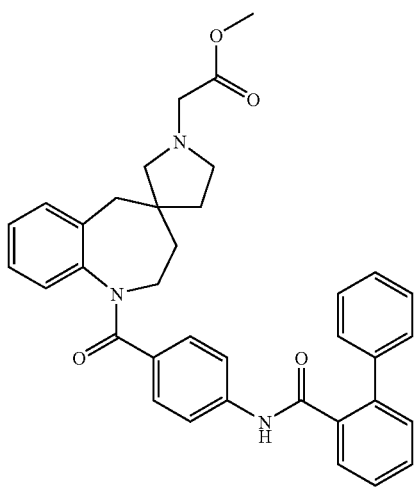

The title compound was prepared from compound 17 and methyl bromoacetate as described in Example 18. ¹H NMR (CDCl₃) δ 7.85(d, J=7Hz, 1H), 7.55-7.4(m, 2H), 7.4-7.3(m, 5H), 7.25-7.2(m, 1H), 7.1-7.05(m, 1H), 7.05-6.95(m, 2H), 6.95-6.85(m, 4H), 6.55-6.45(m, 1H), 4.85-4.65(m, 1H), 3.75 (m, 3H), 3.4-3.25(m, 2H), 3.2-3.2(m, 1H), 3.0-2.7(m, 4H), 2.55-2.45(m, 1H), 1.9-1.75(m, 1H), 1.75-1.6(m, 2H). MS (ES) m/z 574(MH)⁺

Example 23

[1,1'-Biphenyl]-2-carboxamide, N-[4-[(2,3-dihydro-1'-acetic acid-spiro{4H-1-benzazepine-4,3'-pyrrolidin}-1(5H)-yl)carbonyl]phenyl]-, ethyl ester (23)

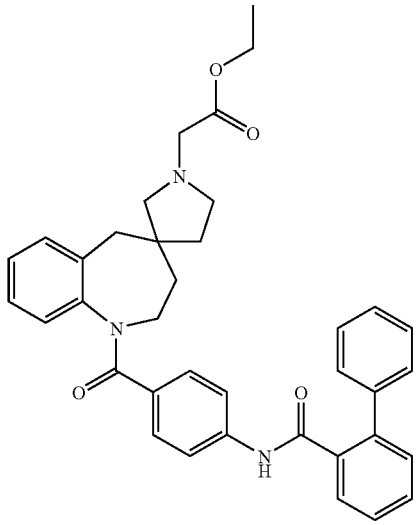

The title compound was prepared from compound 17 and ethyl bromoacetate as described in Example 18. ¹H NMR (CDCl₃) δ 7.85(d, J=7Hz, 1H), 7.55-7.4(m, 2H), 7.4-7.3(m, 5H), 7.25-7.2(m, 1H), 7.1-7.05(m, 1H), 7.05-6.95(m, 2H), 6.95-6.85(m, 4H), 6.55-6.45(m, 1H), 4.85-4.65(m, 1H), 3.4-3.25(m, 2H), 3.2-3.2(m, 1H), 3.0-2.7(m, 4H), 2.55-2.45(m, 1H), 1.9-1.75(m, 1H), 1.75-1.6(m, 2H), 1.3-1.2(m, 3H). MS (ES) m/z 588(MH)⁺

Example 24

[1,1'-Biphenyl]-2-carboxamide, N-[4-[(2,3-dihydro-1'-acetic acid-spiro{4H-1-benzazepine-4,3'-pyrrolidin}-1(5H)-yl)carbonyl]phenyl}- (24)

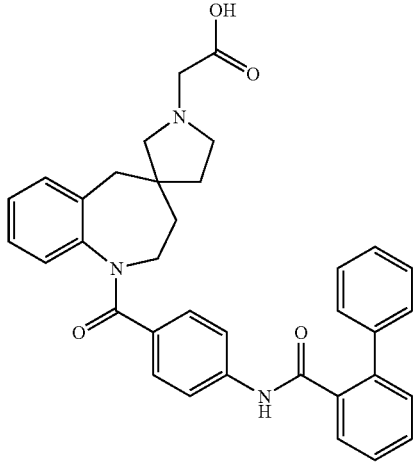

The title compound was prepared from compound 23 by base hydrolysis with 1N NaOH. MS (ES) m/z 560(MH)⁺

Example 25

[1,1'-Biphenyl]-2-carboxamide, N-[4-[(2,3-dihydro-1'-pyruvic acid-spiro{4H-1-benzazepine-4,3'-pyrrolidin}-1(5H)-yl)carbonyl]phenyl}-, ethyl ester (25)

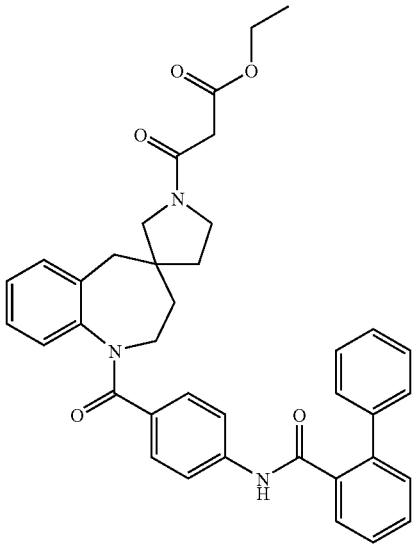

The title compound was prepared from compound 17 and ethyl bromopyruvate as described in Example 18. ¹H NMR (CDCl₃) δ 7.85(d, J=7z, 1H), 7.55-7.4(m, 2H), 7.4-7.3(m, 5H), 7.15-7.05(m, 3H), 7.05-6.85(m, 5H), 6.65(m, J=7Hz, 1H), 4.85-4.65(m, 1H), 4.2 (q, J=7Hz, 2H), 3.7-3.5(m, 2H), 3.45-3.3(m, 2H), 3.25-3.1(m, 2H), 2.95-2.75(m, 1H), 2.75-2.6(m, 1H), 1.8-1.6(m, 2H), 1.3(t, J=7Hz, 3H). MS (ES) m/z 616(MH)⁺

Example 26

[1,1'-Biphenyl]-2-carboxamide, N-[4-[(2,3-dihydro-1'-pyruvic acid-spiro{4H-1-benzazepine-4,3'-pyrrolidin}-1(5H)-yl)carbonyl]phenyl}- (26)

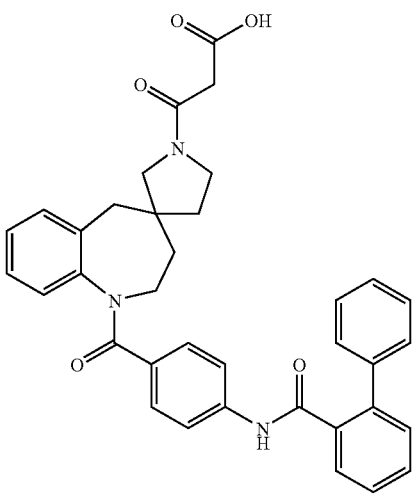

The title compound was prepared from compound 26 by base hydrolysis with 1N NaOH. $^1$H NMR (CDCl$_3$) δ 7.85(d, J=7z, 1H), 7.55-7.4(m, 2H), 7.4-7.3(m, 5H), 7.15-7.05(m, 3H), 7.05-6.85(m, 5H), 6.65(m, J=7Hz, 1H), 4.85-4.65(m, 1H), 3.7-3.5(m, 2H), 3.45-3.3(m, 2H), 3.25-3.1(m, 2H), 2.95-2.75(m, 1H), 2.75-2.6(m, 1H), 1.8-1.6(m, 2H). MS (ES) m/z 588(MH)$^+$ Example 27

[1,1'-Biphenyl]-2-carboxamide, N-[4-[(2,3-dihydro-1'-acetyl-spiro{4H-1-benzazepine-4,3'-pyrrolidin}-1(5H)-yl)carbonyl]phenyl}- (27)

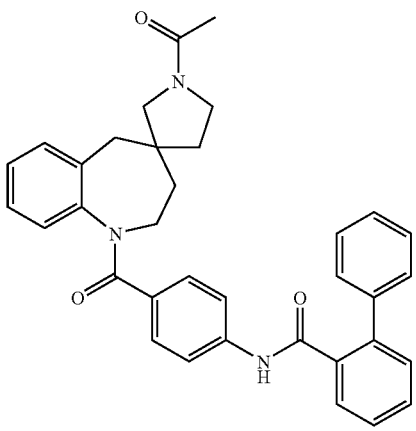

The title compound was prepared from compound 17 and acetyl chloride as described in Example 18. $^1$H NMR (CDCl$_3$) δ 7.85(d, J=7Hz, 1H), 7.55-7.4(m, 2H), 7.4-7.3(m, 5H), 7.15-7.0(m, 3H), 6.95-6.85(m, 5H), 6.65-6.55(d, J=7Hz, 1H), 4.85-4.65(m, 1H), 3.7-3.5(m, 2H), 3.25-3.1(m, 1H), 2.95-2.75(m, 1H), 2.65-2.55(t, J=7Hz, 2H), 2.05(s, 3H), 1.95-1.85(m, 2H), 1.8-1.6(m, 1H), 1.25(t, J=7Hz, 2H). MS (ES) m/z 544(MH)$^+$ Example 28

[1,1'-Biphenyl]-2-carboxamide, N-[4-[(2,3-dihydro-(1'-(2-(dimethylamino)acetyl))spiro{4H-1-benzazepine-4,3'-pyrrolidin}-1(5H)-yl)carbonyl]phenyl]-; (28)

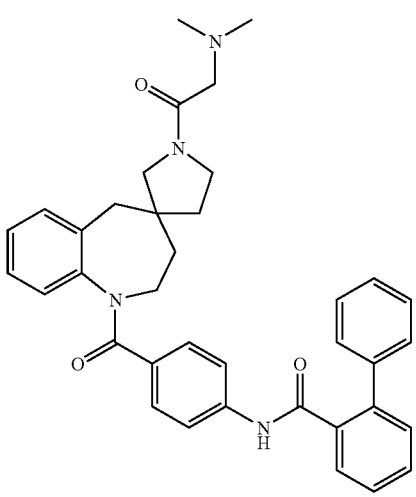

The title compound was prepared from compound 17 and N,N-dimethyl glycine as described in Example 18. $^1$H NMR (CDCl$_3$) δ 7.85(d, J=7Hz, 1H), 7.55-7.4(m, 2H), 7.4-7.3(m, 5H), 7.2-7.0(m, 4H), 7.0-6.85(m, 4H), 6.65-6.55(d, J=7Hz, 1H), 4.85-4.65(m, 1H), 3.7-3.5(m, 2H), 3.4-3.25(m, 1H), 3.2-3.0(m, 2H), 2.95-2.85(m, 1H), 2.7-2.5(m, 1H), 2.35(s, 3H), 2.25(m, 1H), 1.75-1.6(m, 1H), 1.8-1.6(m, 1H), 1.4(t, J=7Hz, 2H). MS (ES) m/z 587(MH)$^+$ Example 29

4-(3-Ethoxycarbonyl-propyl)-5-oxo-1-(4-methylphenylsulfonyl)-2,3,4,5-tetrahydro-1H-benzo[b]azepine-4-carboxylic acid ethyl ester (29)

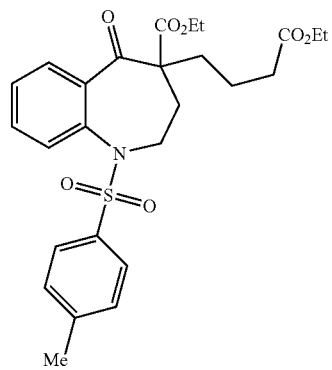

To a solution of 4.67 g (12.1 mmol) of 1 in DMF (24 mL) was added K$_2$CO$_3$ (25.0 g, 18.1 mmol). The resulting suspension was treated with ethyl 4-bromobutyrate (1.90 mL, 13.3 mmol) while stirring mechanically under a nitrogen atmosphere at room temperature. After 18 hours, the reaction mixture was diluted with ethyl acetate (50 mL) and quenched by the addition of aqueous 1N HCl (30 mL). The resulting layers were separated and the organic layer was extracted sequentially with saturated aqueous NaHCO$_3$, water, and brine. The organic extract was subsequently dried over anhydrous MgSO$_4$ and concentrated in vacuo. The residue was purified via column chromatography on silica gel eluting with ethyl acetate/hexanes (3:7) to afford (4.76 g, 79%) of compound 51 as an oil.

Example 30

4-(3-Ethoxycarbonyl-propyl)-1-(4-methylphenylsulfonyl)-2,3,4,5-tetrahydro-1H-benzo[b]azepine-4-carboxylic acid ethyl ester (30)

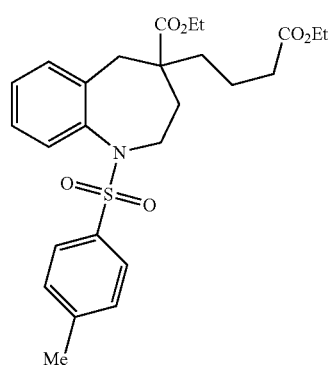

Compound 29 (4.76 g, 9.48 mmol) was dissolved in 45 mL of dry 1,2-dichloroethane, cooled to 5° C., and treated with trifluoroacetic acid (1.3 mL), BF$_3$.Et$_2$O (1.4 mL), anhydrous methanesulfonic acid (3.2 mL) and triethylsilane (5.7 mL). The reaction was allowed to slowly warm to room temperature over 18 hours. The reaction was cooled to 5° C. and cautiously quenched with saturated aqueous NaHCO$_3$ (100 mL). The reaction mixture was extracted with ethyl acetate (100 mL) and the ethyl acetate extract was extracted with saturated aqueous NaHCO$_3$, water, brine (2×), dried over Na$_2$SO$_4$, and concentrated in vacuo to give an oil. This oil was purified by column chromatography on silica gel eluting with hexane/ethyl acetate (17:3) to give 2.43 g (53%) of compound 30 as a colorless oil.

Example 31

Spiro[4H-1-benzazepine-4,1'-cyclopentane]-3'-carboxylic acid, 1,2,3,5-tetrahydro-1-[(4-methylphenyl)sulfonyl]-2'-oxo-, ethyl ester (31)

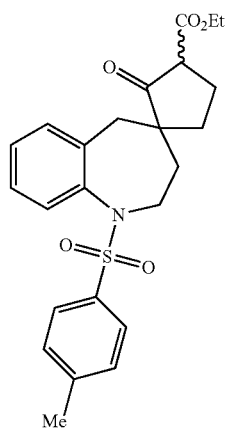

Compound 30 (2.43 g, 4.98 mmol) was dissolved in toluene (25 mL) and treated with potassium tert-butoxide (0.843 g, 7.52 mmol) at room temperature. After 1 hour, the reaction mixture was quenched with aqueous 0.5 N HCl (30 mL) and extracted with ethyl acetate (30 mL). The ethyl acetate extract was washed twice with water, saturated aqueous NaHCO$_3$, water, brine, dried over anhydrous Na$_2$SO$_4$ and concentrate in vacuo. The residue was purified via column chromatography on silica gel eluting with hexane/ethyl acetate (4:1) to give 1.71 g (78%) of 31 as a solid.

Example 32

Spiro[4H-1-benzazepine-4,1'-cyclopentan]-2'-one, 1,2,3,5-tetrahydro-1-[(4-methylphenyl)sulfonyl]- (32)

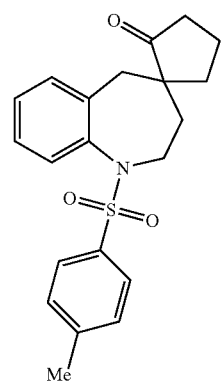

Compound 31 (6.70 g, 15.2 mmol) was combined with ethanol (23 mL), acetic acid (23 mL), and 6 N aqueous HCl (23 mL) and heated at reflux while stirring for 2.5 hours. The reaction mixture was cooled to room temperature and concentrated in vacuo to give 5.36 g (95%) of compound 32.

Example 33

Spiro[4H-1-benzazepine-4,1'-cyclopentan]-2'-one, 1,2,3,5-tetrahydro-1-[(4-methylphenyl)sulfonyl]-, oxime (33)

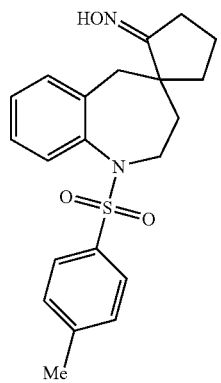

Compound 32 (0.50 g, 1.35 mmol) was combined with ethanol (21 mL), pyridine (4 mL), and hydroxylamine hydrochloride (376 mg, 5.4 mmol) and heated at reflux while stirring for 5 hours. The reaction mixture was cooled to room temperature, concentrated in vacuo and the residue taken up in dichloromethane. The organic layer was extracted with water, dried over anhydrous MgSO$_4$, and concentrated in vacuo to furnish 515 mg (99%) of compound 3 as a clear film.

Example 34

Spiro[4H-1-benzazepine-4,2'-piperidin]-6'-one, 1,2,3,5-tetrahydro-1-[(4-methylphenyl)sulfonyl]- (34)

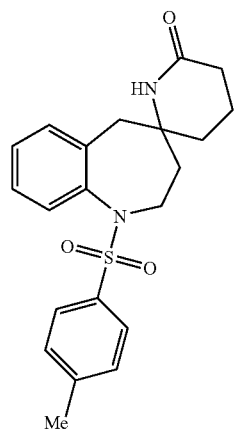

Compound 33 (515 mg, 1.34 mmol) was combined with pyridine (10 mL), 4-dimethylaminopyridine (10 mg, 0.08 mmol), p-toluenesulfonyl chloride (639 mg, 3.35 mmol) and heated at 65° C. while stirring for 3 hours. The reaction mixture was cooled to room temperature, concentrated in vacuo. The residue was taken up in dichloromethane and the organic layer was extracted sequentially with two times 2N aqueous HCl, saturated aqueous NaHCO₃, dried over anhydrous MgSO₄, concentrated in vacuo and purified via column chromatography on silica gel eluting with a gradient of 0-10% methanol in dichloromethane over 60 minutes to afford 361 mg (70%) of compound 34 as a clear film.

Example 35

Spiro[4H-1-benzazepine-4,2'-piperidine], 1,2,3,5-tetrahydro-1-[(4-methylphenyl)sulfonyl]- (35)

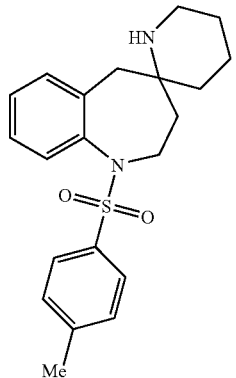

A solution of compound 35 (361 mg, 0.94 mmol) in tetrahydrofuran (7 mL) was treated with 2.0M borane-methyl sulfide complex in tetrahydrofuran (1 mL, 2.0 mmol) and heated at reflux under an atmosphere of argon 1 hour. The reaction material was quenched with water and the organic layer extracted with water, brine, dried over anhydrous MgSO₄, concentrated in vacuo and purified via column chromatography on silica gel eluting with a gradient of 5-10% methanol in dichloromethane over 60 minutes to afford 202 mg (58%) of compound 35 as a foamy white solid.

Example 36

Spiro[4H-1-benzazepine-4,2'-piperidine], 1,2,3,5-tetrahydro-1'-methyl-1-[(4-methylphenyl)sulfonyl]- (36)

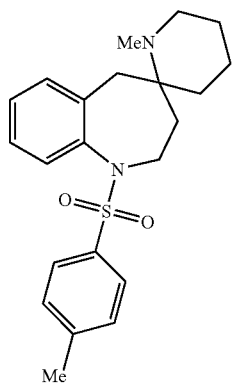

Compound 35 (194 mg, 0.52 mmol) was combined with 37% aqueous formaldehyde solution (2.5 mL), formic acid (0.125 mL), methanol (2.5 mL) and heated at 65° C. while stirring for 18 hours. The reaction mixture was cooled to room temperature, diluted with dichloromethane (10 mL) and quenched with 0.1N aqueous sodium hydroxide (10 mL). The organic layer was separated, dried over anhydrous MgSO₄, concentrated in vacuo to afford 221 mg (quant) of compound 36 as a colorless syrup.

Example 37

Spiro[4H-1-benzazepine-4,2'-piperidine], 1,2,3,5-tetrahydro-1'-methyl- (37)

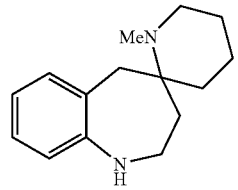

Compound 36 (191 mg, 0.50 mmol) was dissolved in anhydrous methanol (25 mL) and combined with magnesium turnings (0.241 g, 9.90 mmol) and heated at reflux while magnetically stirring under an argon atmosphere over 18 hours. The reaction was cooled to room temperature, filtered through filter agent, and concentrated in vacuo. The residue was triturated 3 times with ethyl acetate and the combined ethyl acetate triturations were filtered through filter agent. The filtrate was extracted with twice with brine, dried over anhydrous Na₂SO₄, and concentrated in vacuo to give 0.095 g (82%) of 37.

Example 38

Benzamide, 2-chloro-N-[4-[(2,3-dihydro-spiro[4H-1-benzazepine-4,2'-piperidin]-1(5H)-yl)carbonyl]phenyl]-5-fluoro- (38)

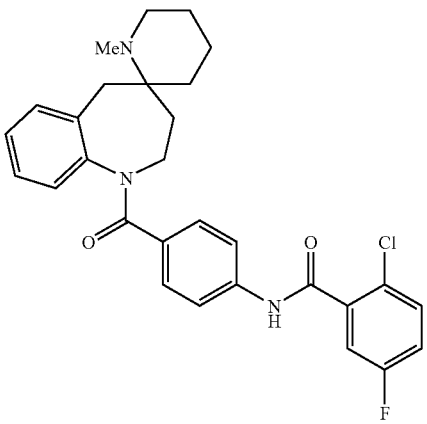

A slurry of compound 4-(2-chloro-5-fluoro-benzoylamino) benzoic acid (126 mg, 0.43 mmol) in dichloromethane (1 mL) was treated with thionyl chloride (1 mL) and heated at reflux under an atmosphere of argon over 18 hours. The reaction mixture was concentrated in vacuo and dissolved in 50 mL of dichloromethane. The resulting solution of acid chloride was added dropwise at 5° C. to a solution of compound 37 (0.095 g, 0.41 mmol), triethylamine (1 mL), and N,N-dimethylformamide (0.05 mL) in dichloromethane (5 mL) while stirring under an argon atmosphere. After 18 hours, the reaction mixture was extracted with saturated aqueous NaHCO$_3$. The organic layer was dried over anhydrous MgSO$_4$, concentrated in vacuo and purified via reverse-phase chromatography on a Kromasil C$_{18}$ column eluting with a gradient of 10-90% acetonitrile in water (0.2% trifluoroacetic acid) over 30 minutes to afford 53.6 mg (19%) of compound 38 as a white powder. $^1$H NMR (300 MHz, CDCl$_3$) δ 1.46-1.92 (overlapping m, 7H), 2.31-2.41(m, 1H), 2.77-3.29 (overlapping m, 5H), 3.32-3.92 (overlapping m, 3H), 5.08(broad m, 1H), 6.77(m, 1H), 7.1-7.53 (overlapping m, 10H); MS (ES) m/z 506(MH)$^+$.

Example 39

Spiro[4H-1-benzazepine-4,2'-piperidine], 1,2,3,5-tetrahydro-1-[(4-methyl phenyl)sulfonyl]-1'-(phenylmethyl)- (39)

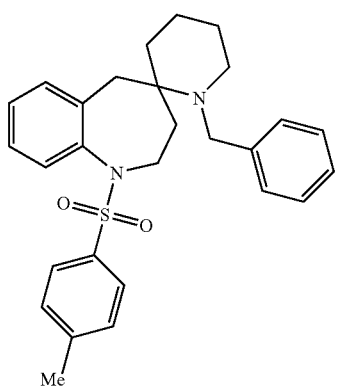

Compound 35 (0.203 g, 0.530 mmol) was combined with benzyl bromide (94 mg, 0.55 mmol), potassium carbonate (146 mg, 1.06 mmol), N,N-dimethylformamide (5 mL) and heated at 70° C. while stirring for 18 hours. The reaction mixture was diluted with ethyl acetate and the organic layer extracted with water, brine, dried over anhydrous Na$_2$SO$_4$, concentrated in vacuo and purified via column chromatography on silica gel eluting with a gradient of 0-25% methanol in dichloromethane over 60 minutes to afford 134 mg (55%) of compound 39 as a colorless oil.

Example 40

Spiro[4H-1-benzazepine-4,2'-piperidine], 1,2,3,5-tetrahydro-1'-(phenylmethyl)- (40)

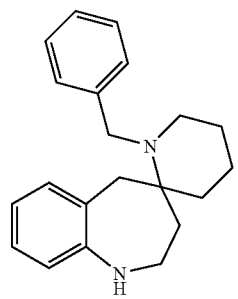

Compound 39 (134 mg, 0.29 mmol) was dissolved in anhydrous methanol (10 mL) and combined with magnesium turnings (0.141 g, 5.80 mmol) and heated at reflux while magnetically stirring under an argon atmosphere over 15 hours. The reaction was cooled to room temperature, filtered through filter agent, and concentrated in vacuo. The residue was triturated 3 times with ethyl acetate and the combined ethyl acetate triturations were filtered through filter agent. The filtrate was extracted with twice with brine, dried over anhydrous Na$_2$SO$_4$, concentrated in vacuo to give 0.033 g (37%) of 40 as a clear oil.

Example 41

[1,1'-Biphenyl]-2-carboxamide, N-{4-[(2,3-dihydro-1'-(phenylmethyl)spiro[4H-1-benzazepine-4,2'-piperidin]-1(5H)-yl)carbonyl]phenyl}- (41)

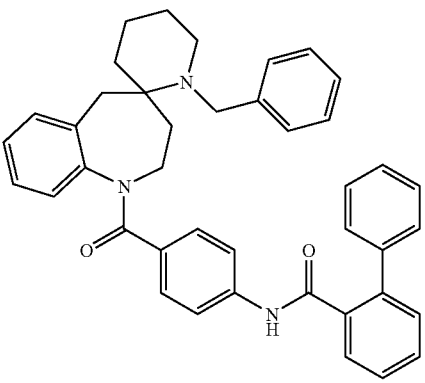

To a slurry of 0.033 g (0.12 mmol) of 4-[([1,1'-biphenyl]-2-ylcarbonyl)amino]benzoic acid in dichloromethane (5 mL) was added was added N,N-dimethylformamide (0.02 mL), thionyl chloride (1 mL) while stirring at room temperature under an argon atmosphere. After 18 hours, the resulting solution was concentrated in vacuo, dissolved in dry toluene, concentrated in vacuo, and dissolved in 2 mL of dichloromethane. The resulting solution of acid chloride was added dropwise to a solution of compound 40 (0.033 g, 0.11 mmol), triethylamine (1 mL), and 0.02 mL of N,N-dimethylformamide in 5 mL of dichloromethane while stirring at room temperature. After 72 hours, the reaction mixture was quenched with saturated aqueous NaHCO$_3$ and extracted with ethyl acetate. The ethyl acetate layer was extracted with saturated aqueous NaHCO$_3$, brine, dried over anhydrous Na$_2$SO$_4$, and concentrated in vacuo. The residue was purified via thin layer chromatography on silica gel eluting with hexane/ethyl acetate (1:1) to furnish 41.

Example 42

[1,1'-Biphenyl]-2-carboxamide, N-{4-[(2,3-dihydrospiro[4H-1-benzazepine-4,2'-piperidin]-1(5H)-yl)carbonyl]phenyl}- (42)

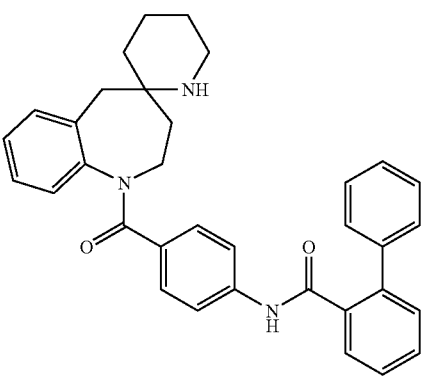

Compound 41 was dissolved in anhydrous methanol (5 mL), combined with palladium on carbon (4 mg) and shaken under a 55 psi hydrogen atmosphere over 7 hours. The reaction mixture was filtered through filter agent, concentrated in vacuo and purified via reverse-phase chromatography on a Kromasil $C_{18}$ column eluting with a gradient of 30-90% acetonitrile in water (0.2% trifluoroacetic acid) over 30 minutes to afford 26.9 mg (32%) of compound 42 as a white powder. $^1$H NMR (300 MHz, CDCl$_3$) δ 1.31-2.19 (overlapping m, 10H), 3.12-4.40 (overlapping m, 4H), 6.77-7.60 (overlapping m, 17H); MS (ES) m/z 516(MH)$^+$.

Example 43

Benzamide, 2-methyl-N-[4-{(2,3-dihydro-1'-benzyl-spiro[4H-1-benzazepine-4,3-pyrrolidin}-1(5H)-yl)carbonyl}pyridyl]-5-fluoro (43)

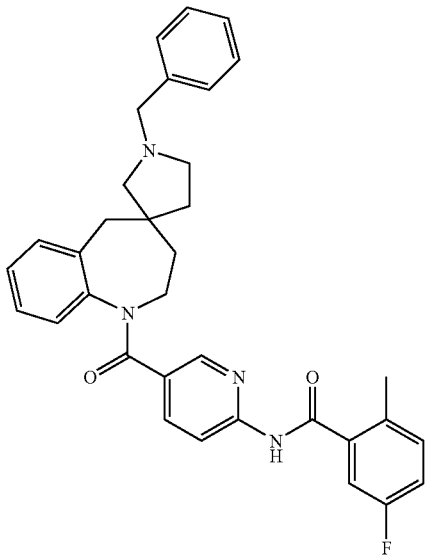

The title compound was prepared from compound 15 and 6-(5-fluoro-2-methyl-benzoylamino)-nicotinoyl chloride (*Bioorg. Med. Chem. Lett.*, 1999, 9, 1737-1740) as described in Example 41. $^1$H NMR (CDCl$_3$) 8.35(br s, 1H), 8.1(m, 1H), 8.05(br s, 1H), 7.55-7.45(m, 1H), 7.35-6.95(m, 10H), 4.85-4.6(m, 1H), 3.7-3.55(m, 2H), 3.15-3.1(m, 1H), 2.8-2.75(m, 3H), 2.65-2.6(m, 1H), 2.4(m, 3H), 1.85-1.8(m, 2H), 1.4-1.25 (m, 2H). MS (ES) m/z 549(MH)$^+$ Example 44

Benzamide, N-[4-{(2,3-dihydro-1'-methyl-spiro[4H-1-benzazepine-4,3-piperidin}-1(5H)-yl)carbonyl}phenyl] (44)

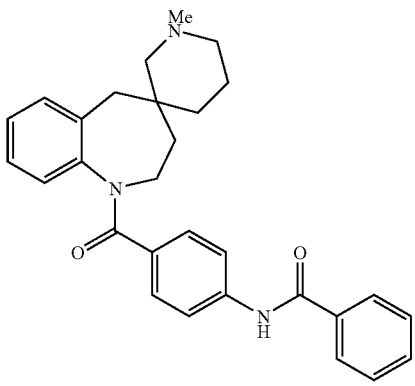

The title compound was prepared from compound 7 and benzoyl chloride. $^1$H NMR (CDCl$_3$) δ 7.95(br s, 1H), 7.85(d, J=7Hz, 2H), 7.5-7.4(m, 4H), 7.2-7.1(m, 3H), 7.1-7.0(m, 1H), 6.95-6.9(m, 1H), 6.6-6.5(m, 1H), 5.8-5.5(br m, 1H), 3.2-3.0 (m, 2H), 2.9-2.8(m, 2H), 2.75-2.65(m, 1H), 2.4-2.2(m, 4H), 2.1(br s, 1H), 1.9-1.8(m, 2H), 1.75-1.6(m, 2H), 1.4-1.2(m, 2H), 0.95(m, 1H). MS (ES) m/z 486(MH)$^+$ Biological Example 1

(A) In-Vitro Binding Assay

Assay buffer is 50 mM Tris-Cl, 5 mM MgCl$_2$, 0.1% BSA (pH 7.5) containing 5 µg/ml of aprotinin, leupeptin, pepstatin, 50 µg/ml bacitracin, and 1 mM Pefabloc (4-(2-Aminoethyl)-benzenesulfonyl fluoride, hydrochloride manufactured by Roche Diagnostics Corporation, Indianapolis, Ind. and distributed by Boehringer Mannheim). H3 vasopressin is $^3$H-arginine-8-vasopressin (NEN Life Sciences, Boston, Mass.; 68.5 Ci/mmol, final concentration in assay is 0.65-0.75 nM). Into wells of 96-well round bottom polypropylene plates are added buffer, test compound, membrane (containing human V1a or V2 receptor), and H3 vasopressin. The reaction plates are allowed to sit at room temperature for one hour. The samples are filtered through Unifilter GF/C plates (PerkinElmer Life Sciences, Boston, Mass.) presoaked in 0.3 polyethyleneimine. The plates are washed 5 times with cold physiological saline containing 0.05% Tween 20. After drying, the bottom of the filter plates $$\% \text{ inhibition} = 100 - 100 \times \frac{\text{peak response after drug}}{\text{peak response before drug}}$$

are sealed and 0.025 ml of Microscint-20 (Packard Instrument Co, Meriden, Conn.) is added to each filter. The top of the plate is sealed, and the plate is counted. Non-specific binding is determined by the addition of 1.25 µM arginine-8-vasopressin in those wells. % Inh. is calculated as follows:

(B) V1a Vasopressin Receptor Functional Activity

The V1a receptor is a G-protein coupled receptor, which upon activation triggers an increase in intracellular calcium mobilization. To evaluate compounds for their functional V1a receptor activity, HEK-293 cells were transfected with the human V1a receptor (V1a-HEK cells). HEK-293 cells were grown in DMEM (Dulbecco's modified Eagle Media) supplemented with 10% FBS and glutamine. HEK-cells were passed biweekly by trypsinization and seeded into 96 well plates at 33,000 cells per well. HEK-293 cells were transfected with human V1a receptor DNA using DMRIE-C reagent from Life Technologies (Carlsbad, Calif.). Stable lines were generated by selecting cells grown in culture media containing geneticin. After growing in Packard Clear-View black 96 well plates for 4-6 days, V1a-HEK cells were loaded with the calcium-sensitive fluorescence dye, FLUO-3 AM. Changes in intracellular calcium mobilization were measured by quantitating intracellular fluorescence using FLIPR (Fluorometric Imaging Plate Reader; Molecular Devices, Sunnyvale, Calif.). Test compounds were first added to the cells and the resulting changes in fluorescence measured to detect receptor agonistic activity. Five minutes later the cells were challenged with vasopressin to test compounds for their antagonistic activity. Receptor antagonists inhibit the ability of vasopressin to stimulate increases in intracellular fluorescence. IC$_{50}$'s were calculated.

Biological Example 2

V2 Vasopressin Receptor Functional Activity

The V2 receptor is also a G-protein coupled receptor which when activated induces an increase in cAMP turnover. Antagonism against the V2 receptor is determined by measuring cAMP accumulation in transfected HEK-293 cells expressing the human V-2 receptor (V2-HEK cells). Compounds are tested for their ability to block the stimulatory effects of vasopressin on cAMP accumulation. The cell content of cAMP is measured by radioimmunoassay using NEN flashplates.

Biological Example 3

Reversal of Vasopressin-Induced Hypertension in Rats

The anti-hypertensive activity of a compound is assessed using an anesthetized model of vasopressin-induced hypertension. Male Long Evans, normotensive rats of between 350 and 450 g in body weight are anesthetized with pentobarbital (35 mg/kg, ip) and maintained throughout the procedure with an ip infusion of 10 mg/kg/hr. Arginine vasopressin (AVP) is infused at 30 ng/kg/min, iv, to induce a stable hypertensive state (ca. 50 mm Hg increase in mean arterial blood pressure). Compounds of interest are administered in an ascending dose fashion and the maximum decrease in mean arterial blood pressure is recorded. An $ED_{50}$ is determined from the linear portion of the dose-response relationship for each animal.

Biological Example 4

Several animal models are believed to mimic various components of diabetic nephropathy in humans, in particular, the streptozotocin-induced model of type 1 diabetes in rats, the db/db genetic mouse model of type 2 diabetes and the 5/6 nephrectomy model of renal failure in rats. Compounds are evaluated in the streptozotocin diabetic model by administering the compound at 1, 3 or 10 mg/kg/day for 12 weeks and monitored at several endpoints during the study that are indicative of diabetic kidney disease, including reduced urine albumin, serum creatinine levels and levels of various cytokines in urine. At the end of the study, morphologic changes in the kidney are evaluated histologically for comparison to normal kidneys. Similar studies are performed in the other two models to confirm activity.

Biological Example 5

Argenine-vasopressin (AVP) levels are dramatically elevated following ischemic stroke and head injury and contribute to the tissue inflammatory response. AVP receptor antagonists have been shown to block development of cerebral edema following traumatic brain injury and ischemic stroke by regulating water and electrolyte transport across the cerebrovascular endothelium (via endothelial V1a receptor inhibition) and by promoting diuresis (via renal V2 receptors). Additional neuroprotective actions of AVP receptor antagonists may be mediated by inhibition of neuronal V1a receptors. Thus, compounds of this invention may be useful in ischemic stroke and traumatic brain injury. V1a/V2 antagonists may reduce the post-ischemia inflammatory response and reduce the volume of brain tissue infarction following ischemic stroke. As many of the neuroprotective and anti-edema actions of AVP receptor antagonists are mediated at the level of the cerebrovascular endothelium or kidney, it is not essential that compounds cross the blood brain barrier. However, as noted above, CNS penetration may add benefit by limiting actions of AVP at neuronal V1a receptors.

The pharmacokinetic properties of a compound may be determined in order to optimize plasma half-life and optimal dosing regimen. This includes the ability of these compounds to cross the blood-brain barrier, and direct measurement of drug concentrations and half-life in brain tissue. The neuroprotective and anti-edema properties of these compounds can be determined with a rodent model of embolic stroke. In this model, an aliquot of the animal's blood is removed and refrigerated overnight to allow a thrombin-rich clot to form. This clot is then placed surgically at the origin of the middle cerebral artery and left in place for 2-4 hrs to produce prolonged cerebral ischemia. At this point the clot may be left in place permanently or the clot may be lysed using intravenous administration of recombinant tissue plasminogen activator (rt-PA) to allow reperfusion. The vasopressin receptor antagonists of this invention may be administered intravenously at various times following clot placement and may be given as a bolus dose, a bolus dose followed by continuous intravenous infusion or continuous intravenous infusion alone. Compound may be given at times ranging from two hours to one week following onset of ischemia to define the optimal treatment window. The acute intravenous dosing may also be followed by oral administration of the compound to determine the optimal treatment duration.

The vasopressin receptor antagonists of this invention may be profiled in a rodent model of traumatic brain injury. This model requires opening a cranial window to expose the dura matter. A controlled, measured weight is then dropped on the dura to induce injury. This model is well characterized and produces a defined pattern of neuronal cell loss and inflammation.

Edema, inflammation and neuroprotection may be determined using one or more of the following approaches: Animals may be euthanized at various time points following ischemia, from 24 hrs to four weeks, and the volume of infarction and brain edema may be measured using standard histological and histochemical methods. Animals may also be subjected to MRI imaging so that the evolution of infarction and edema can be measured within the same animal. Finally, histological and histochemical measurements of blood-brain barrier integrity and infiltration of inflammatory cells (e.g., monocytes, macrophages, microglial cells) may be performed and used for quantitative analyses.

Finally, all animals may be evaluated in a comprehensive series of behavioral assays to evaluate the effects of vasopressin receptor antagonists on neurological function and behavior. These behavioral assessments may include a global neurological assessment, evaluation of motor asymmetry and assessment of sensorimotor integration using assays such as the foot-fault, Rotarod and beam-balance tests.

Table I sets forth the vasopressin receptor binding data and V1a/V2 vasopressin receptor functional activity of some compounds of the instant invention.

TABLE I

| Compound # | V1a (binding) µM | V1a (functional) µM (IC50) | V2 (binding) µM | V2 (functional) µM (IC50) |
|---|---|---|---|---|
| 8 | 0.012 | 0.01 | 52%* | 0.46 |
| 10 | 0.015 | 0.08 | 0.029 | 0.064 |

TABLE I-continued

| Compound # | V1a (binding) μM | V1a (functional) μM (IC50) | V2 (binding) μM | V2 (functional) μM (IC50) |
|---|---|---|---|---|
| 18 | 66%* | — | 70%* | — |
| 22 | 66%* | 0.40 | 0.11 | 0.049 |
| 23 | 75%* | 0.78 | 58%* | 0.673 |
| 25 | 35%* | — | 77%* | 0.306 |
| 26 | 23%* | — | 83%* | 0.272 |
| 27 | 61%* | 0.21 | 78%* | 0.182 |
| 28 | 0.26 | — | 0 | — |

*Percent inhibition at 0.2 μM

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound having the structure shown in Formula I:

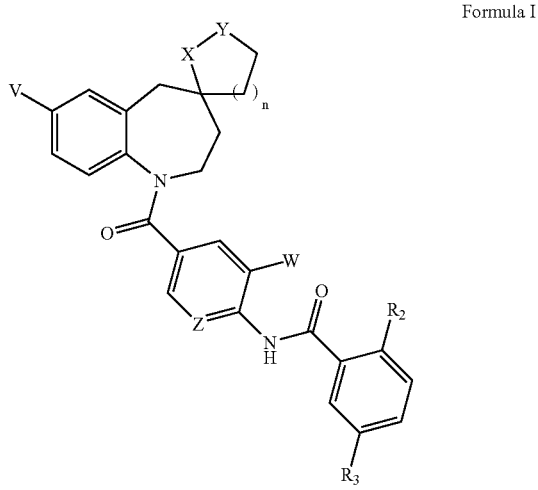

Formula I or pharmaceutically acceptable salts, racemic mixtures, diastereomers and enantiomers thereof wherein:
one of X and Y is $CH_2$ and the other is $NR_1$;
Z is CH or N;
V is H, $C_{1-3}$ alkyl, $C_{1-3}$ alkoxy or halogen;
n=1 or 2,
W is H, $C_{1-3}$ alkoxy; or hydroxyl;
$R_1$ is H, $C_{1-5}$ alkyl, arylalkyl, $C_{3-5}$ cycloalkyl, $-CH_2-C(O)OR_5$, $-C(O)R_4$, $-C(O)(CH_2)_m-N(R_6)(R_6)$, or $-C(O)-CH_2-C(O)OR_5$, where $R_4$ is $C_{1-3}$ alkyl, $R_5$ is H or $C_{1-3}$ alkyl and m is 1 to 3;
$R_2$ is H, halogen, $C_{1-5}$ alkyl, $C_{1-3}$ alkoxy or aryl;
$R_3$ is H, halogen, $C_{1-5}$ alkyl, $C_{1-3}$ alkoxy or aryl; with the proviso that at least one of $R_1$, $R_2$ and $R_3$ is not H; and
the $R_6$ moieties can be the same or different, each being independently selected from the group consisting of H, $C_{1-6}$alkyl, and $C_{3-5}$ cycloalkyl; or alternatively two $R_6$ moieties can be linked together with the N to which they are attached to form a 5 to 6 membered heterocyclyl.

2. A compound of claim 1, wherein $R_1$ is methyl, ethyl, benzyl, cyclopentyl, $-CH_2-C(O)OR_5$, $-C(O)R_4$, $-C(O)CH_2-N(CH_3)_2$, $-C(O)(CH_2)_m$-5 to 6 membered heterocyclyl or $-C(O)-CH_2-C(O)OR_5$.

3. A compound of claim 1, wherein $R_2$ is H, phenyl, $CH_3$, $-OCH_3$, F or Cl.

4. A compound of claim 3, wherein $R_2$ is phenyl.

5. A compound of claim 3, wherein $R_2$ is phenyl and $R_3$ is H.

6. A compound of claim 1, wherein n is 1.

7. A compound of claim 1, wherein $R_2$ is phenyl; n is 1; and $R_3$ is H.

8. A compound of claim 1, wherein $R_3$ is F.

9. A compound of claim 1, wherein Z is CH.

10. A compound of claim 1, wherein Z is N.

11. A compound of claim 1, wherein V is H, $CH_3$, $-OCH_3$, F or Cl.

12. A compound of claim 1, wherein V is H.

13. A compound of claim 1, wherein X is $CH_2$.

14. A compound of claim 1 selected from the group consisting of:

Benzamide, 2-chloro-N-[4-{(2,3-dihydro-1'-methyl-spiro[4H-1-benzazepine-4,3-piperidin]-1(5H)-yl)carbonyl}phenyl]-5-fluoro;

[1,1'-Biphenyl]-2-carboxamide, N-[4-[(2,3-dihydro-1'-ethyl-spiro{4H-1-benzazepine-4,3'-piperidin}-1(5H)-yl)carbonyl]phenyl]-;

[1,1'-Biphenyl]-2-carboxamide, N-[4-[(2,3-dihydro-1'-methyl-spiro{4H-1-benzazepine-4,3'-piperidin}-1(5H)-yl)carbonyl]phenyl]-;

[1,1'-Biphenyl]-2-carboxamide, N-[4-[(2,3-dihydro-1'-benzyl-spiro{4H-1-benzazepine-4,3'-pyrrolidin}-1(5H)-yl)carbonyl]phenyl]-;

[1,1'-Biphenyl]-2-carboxamide, N-[4-[(2,3-dihydro-spiro{4H-1-benzazepine-4,3'-pyrrolidin}-1(5H)-yl)carbonyl]phenyl]-;

[1,1'-Biphenyl]-2-carboxamide, N-[4-[(2,3-dihydro-1'-cyclopropyl -spiro{4H-1-benzazepine-4,3'-pyrrolidin}-1(5H)-yl)carbonyl]phenyl]-;

[1,1'-Biphenyl]-2-carboxamide, N-[4-[(2,3-dihydro-1'-methyl -spiro{4H-1-benzazepine-4,3'-pyrrolidin}-1(5H)-yl)carbonyl]phenyl]-;

[1,1'-Biphenyl]-2-carboxamide, N-[4-[(2,3-dihydro-1'-isopropyl -spiro{4H-1-benzazepine-4,3'-pyrrolidin}-1(5H)-yl)carbonyl]phenyl]-;

[1,1'-Biphenyl]-2-carboxamide, N-[4-[(2,3-dihydro-1'-acetic acid-spiro{4H-1-benzazepine-4,3'-pyrrolidin}-1(5H)-yl)carbonyl]phenyl]-, methyl ester;

[1,1'-Biphenyl]-2-carboxamide, N-[4-[(2,3-dihydro-1'-acetic acid-spiro{4H-1-benzazepine-4,3'-pyrrolidin}-1(5H)-yl)carbonyl]phenyl]-, ethyl ester;

[1,1'-Biphenyl]-2-carboxamide, N-[4-[(2,3-dihydro-1'-acetic acid-spiro{4H-1-benzazepine-4,3'-pyrrolidin}-1(5H)-yl)carbonyl]phenyl]-;

[1,1'-Biphenyl]-2-carboxamide, N-[4-[(2,3-dihydro-1'-acetyl-spiro{4H-1-benzazepine-4,3'-pyrrolidin}-1(5H)-yl)carbonyl]phenyl]-;

[1,1'-Biphenyl]-2-carboxamide, N-[4-[(2,3-dihydro-(1'-(2-(dimethylamino)acetyl))spiro{4H-1-benzazepine-4,3'-pyrrolidin}-1(5H)-yl)carbonyl]phenyl]-;

[1,1'-Biphenyl]-2-carboxamide, N-[4-[(2,3-dihydrospiro[4H-1-benzazepine-4,2'-piperidin]-1(5H)-yl)carbonyl]phenyl]-;

Benzamide, 2-methyl-N-[4-{(2,3-dihydro-1'-benzyl-spiro[4H-1-benzazepine-4,3-pyrrolidin]-1(5H)-yl)carbonyl}pyridyl]-5-fluoro; and Benzamide, N-[4-{(2,3-dihydro-1'-methyl-spiro[4H-1-benzazepine-4,3-piperidin]-1(5H)-yl)carbonyl}phenyl].

15. A V<sub>1a</sub> selective compound of claim 1, wherein the compound is
Benzamide, N-[4-{(2,3-dihydro-1'-methyl-spiro[4H-1-benzazepine-4,3-piperidin]-1(5H)-yl) carbonyl}phenyl].

16. A compound of claim 1 selected from the group consisting of:
Benzamide, 2-methyl-N-[4-{(2,3-dihydro-1'-methyl-spiro[4H-1-benzazepine-4,3-piperidin]-1(5H)-yl) carbonyl}phenyl]-5-fluoro;
Benzamide, 2-fluoro-N-[4-{(2,3-dihydro-1'-methyl-spiro[4H-1-benzazepine-4,3-piperidin]-1(5H)-yl) carbonyl}phenyl]-5-fluoro;
Benzamide, 2-methoxy-N-[4-{(2,3-dihydro-1'-methyl-spiro[4H-1-benzazepine-4,3-piperidin]-1(5H)-yl) carbonyl}phenyl]-5-fluoro;
Benzamide, 2-methyl-N-[4-{(2,3-dihydro-1'-methyl-spiro[4H-1-benzazepine-4,3-piperidin]-1(5H)-yl) carbonyl}phenyl]; and
Benzamide, 2-fluoro-N-[4-{(2,3-dihydro-1'-methyl-spiro[4H-1-benzazepine-4,3-piperidin]-1(5H)-yl) carbonyl}phenyl].

17. A compound of claim 1 selected from the group consisting of:
Benzamide, 2-chloro-N-[4-{(2,3-dihydro-1'-methyl-spiro[4H-1-benzazepine-4,3-piperidin]-1(5H)-yl) carbonyl}phenyl]-5-fluoro;
[1,1'-Biphenyl]-2-carboxamide, N-[4-[(2,3-dihydro-1'-methyl-spiro{4H-1-benzazepine-4,3'-piperidin}-1(5H)-yl)carbonyl]phenyl]-; and
Benzamide, N-[4-{(2,3-dihydro-1'-methyl-spiro[4H-1-benzazepine-4,3-piperidin]-1(5H)-yl) carbonyl}phenyl].

18. A compound according to claim 1 in purified form.

19. A pharmaceutical composition comprising at least one compound of claim 1, in combination with at least one pharmaceutically acceptable carrier or excipient.

20. A pharmaceutical composition comprising at least one compound of claim 14, in combination with at least one pharmaceutically acceptable carrier or excipient.

21. A method for treating a disease or condition mediated by vasopressin, said method comprising the step of administering to a patient in need of such treatment a therapeutically effective amount of a composition comprising at least one compound according to claim 1, wherein said disease or condition is selected from inner ear disorders, hypertension, congestive heart failure, cardiac insufficiency, coronary vasospasm, cardiac ischemia, liver cirrhosis, renal vasospasm, renal failure, diabetic nephropathy, hyponatremia, cerebral edema, cerebral ischemia, stroke, thrombosis, water retention, aggression, obsessive-compulsive disorders, dysmenorrhea, nephrotic syndrome, anxiety and central nervous injuries.

22. The method of claim 21 wherein said condition is congestive heart failure, or cardiac insufficiency.

23. The method of claim 21, wherein said condition is hyponatremia.

24. The method of claim 21 wherein said condition is hypertension.

25. A process for making a pharmaceutical composition comprising mixing any of the compounds according to claim 1 and a pharmaceutically acceptable carrier.

* * * * *